(12) United States Patent
Gribben et al.

(10) Patent No.: US 7,592,007 B2
(45) Date of Patent: *Sep. 22, 2009

(54) METHODS OF INHIBITING T CELL PROLIFERATION OR IL-2 ACCUMULATION WITH CTLA-4 SPECIFIC ANTIBODIES

(75) Inventors: John G. Gribben, Brookline, MA (US); Gordon J. Freeman, Brookline, MA (US); Lee M. Nadler, Newton, MA (US); Paul Rennert, Holliston, MA (US); Cindy L. Jellis, Londonderry, NH (US); Edward Greenfield, Randolph, MA (US); Gary S. Gray, Brookline, MA (US)

(73) Assignees: Dana-Farber Cancer Institute, Inc., Boston, MA (US); Genetics Institute, LLC, Cambridge, MA (US)

( * ) Notice: Subject to any disclaimer, the term of this patent is extended or adjusted under 35 U.S.C. 154(b) by 711 days.

This patent is subject to a terminal disclaimer.

(21) Appl. No.: 10/732,847

(22) Filed: Dec. 9, 2003

(65) Prior Publication Data
US 2004/0202650 A1    Oct. 14, 2004

Related U.S. Application Data

(62) Division of application No. 08/253,783, filed on Jun. 3, 1994, now Pat. No. 6,719,972.

(51) Int. Cl.
*A61K 39/395* (2006.01)
*C07K 16/28* (2006.01)

(52) U.S. Cl. .............. 424/154.1; 424/130.1; 424/133.1; 424/134.1; 424/139.1; 424/141.1; 424/143.1; 424/144.1; 424/145.1; 424/153.1; 424/173.1; 530/387.1; 530/387.3; 530/388.1; 530/388.2; 530/388.22; 530/388.7; 530/388.73; 530/388.75

(58) Field of Classification Search ....................... None
See application file for complete search history.

(56) References Cited

U.S. PATENT DOCUMENTS 5,434,131 A    7/1995  Linsley
6,719,972 B1 *  4/2004  Gribben et al. .......... 424/154.1

FOREIGN PATENT DOCUMENTS

WO    WO-93/00431     1/1993
WO    WO-93/19767    10/1993
WO    WO-94/03202     2/1994

OTHER PUBLICATIONS

Wadman, Nature, 440: 388-389, 2006.*
Hopkin, Nature, 440: 855-856, 2006.*
Daikh et al., J. Leukoc. Biol. 62: 156-162, 1997.*
Tisch et al., PNAS 91: 437-438, 1994.*
Krummel et al. J Exp Med 183: 2533-2540 (1996).
Bluestone Immunity 2: 555-559 (1995).
Rudin et al. Curr. Opin. Hematol. 3: 35-40 (1996).
Yi-Qun et al. Intl. Immunol. 8: 37-44 (1996).
Blazar et al. J. Immunol. 157: 3250-3259 (1996).
Kahan Curr. Opin. Immunol. 4: 553-560 (1992).
Gribben et al. PNAS 92: 811-815 (1995).
Walunas et al. J Exp Med 183: 2541-2550 (1996).
Perrin et al. J. Neuroimmunology 65: 31-39 (1996).
Paul (ED) Fundamental Immunology Raven Press NY 1993 p. 242.
Coyle et al. Nature Immunology 2: 203-209 (2001).
Skulnick et al. Trends Biotech. 18: 34-39 (2000).
Ngo et al. in the Protein Folding Problem and Tertiary Structure Prediction 1994 Merz et al. (ED) Birkhauser, Boston MA, pp. 433, 492-495.
Mueller Current Biology 10: 12227-12230 (2000).
Yang et al. J. Exp. Med. 168: 1457-1468 (1988).
Lindsten, T., et al., (1993) "Characterization CTLA-4 Structure and Expression on Human T Cells", The Journal of Immunology, vol. 151, No. 7, pp. 3489-3499.
Harper, K., et al., (1991) "CTLA-4 and CD28 Activated Lymphocyte Molecules are Closely Related in Both Mouse and Human as to Sequence, Message Expression, Gene Structure, and Chromosomal Location", The Journal of Immunology, vol. 147, No. 3, pp. 1037-1044.
Jellis, C.L., et al., (1993) "Defining critical residues in the epitope for a HIV-neutralizing monoclonal antibody using phage display and peptide array technologies", Gene, vol. 137, pp. 63-68.
Linsley, P.S., et al., (1992) "Coexpression and Functional Cooperation of CTLA-4 and CD28 on Activated T Lymphocytes", J. Exp. Med., vol. 176, pp. 1595-1604.
Darzynkiewicz, Z., et al., (1992) "Features of Apoptic Cells Measured by Flow Cytometry", Cytometry, vol. 13, pp. 795-808.

(Continued)

*Primary Examiner*—Phillip Gambel
(74) *Attorney, Agent, or Firm*—Foley Hoag LLP

(57) ABSTRACT

Isolated ligands which bind a molecule expressed on the surface of T cells and induce antigen specific apoptosis in activated T cells are disclosed. Preferably, the T cell surface molecule is CTLA4 and the ligand is a monoclonal anti-CTLA4 antibody that binds to an epitope of CTLA4 distinct from the binding sites of B7-1 and B7-2. Upon binding of the antibody to CTLA4 on an activated T cell, in the presence of an antigenic signal, antigen specific apoptosis is induced. The invention also describes a novel natural CTLA4 ligand, distinct from B7-1 and B7-2, which mediates induction of apoptosis. Pharmaceutical compositions of anti-CTLA4 antibodies or other isolated CTLA4 ligands which can be administered to subjects to induce T cell apoptosis, thereby clonally deleting antigen specific T cells, such as alloreactive T cells in transplantation situations or autoreactive T cells in autoimmune disorders, are also disclosed. Methods for inducing T cell apoptosis in vitro with an anti-CTLA4 antibody or other ligand of the invention together with an antigen specific signal are also disclosed, e.g., for use in purging alloreactive T cells from donor bone marrow prior to bone marrow transplantation to inhibit graft versus host disease.

4 Claims, 2 Drawing Sheets

OTHER PUBLICATIONS

Freeman, G.J., et al., (1992) "CTLA-4 and CD28 mRNA are Coexpressed in most T Cells after Activation", The Journal of Immunology, vol. 149, No. 12, pp. 3795-3801.

Hardin, J.A., et al., (1992) "A simple fluorescence method for surface antigen phenotyping of lymphocytes undergoing DNA fragmentation", Journal of Immunological Methods, vol. 154, pp. 99-107.

Linsley, P.S., et al., (1991) "CTLA-4 Is a Second Receptor for the B Cell Activation Antigen B7", J. Exp. Med., vol. 164, pp. 561-569.

Dariavach, P., et al., (1988) "Human Ig superfamily CTLA-4 gene: chromosomal localization and identity of protein sequence between murine and human CTLA-4 cytoplasmic domains", Eur. J. Immunol., vol. 18, pp. 1901-1905.

Brunet, Jean-Francois, et al., (1987) "A new member of the immunoglobulin superfamily—CTLA-4", Nature, vol. 328, pp. 267-270.

Kuntz et al. Science 257: 1078-1082 (1992).

Nagata, S. et al., (1995) "The Fas Death Factor", Science, vol. 267 pp. 1449-1456.

Boussiotis, V. et al., (1993) "Activated Human B Lymphocytes Express Three CTLA-4 Counterreceptors that Costimulate T-cell Activation", PNAS, vol. 90, pp. 11059-11063.

Page, D. M. et al. Two signals are required for negative selection of CD4+CD8+ thymocytes. J Immunol. Aug. 15, 1993;151(4):1868-80.

Harding, F. A. et al. CD28-mediated signalling co-stimulates murine T cells and prevents induction of anergy in T-cell clones. Nature. Apr. 16, 1992;356(6370):607-9.

Freeman, G. J. et al. Cloning of B7-2: a CTLA-4 counter-receptor that costimulates human T cell proliferation. Science. Nov. 5, 1993;262(5135):909-11.

Hathcock, K. S. et al. Identification of an alternative CTLA-4 ligand costimulatory for T cell activation. Science. Nov. 5, 1993;262(5135):905-7.

Dariavach P et al., "Human Ig superfamily CTLA-4 gene: chromosomal localization and identity of protein sequence between murine and human CTLA-4 cytoplasmic domains," Eur. J. Immunol., 18(12):1901-1905, 1988.

* cited by examiner

METHODS OF INHIBITING T CELL PROLIFERATION OR IL-2 ACCUMULATION WITH CTLA-4 SPECIFIC ANTIBODIES

RELATED APPLICATIONS

This application is a divisional of U.S. Ser. No. 08/253,783, filed Jun. 3, 1994, now U.S. Pat. No. 6,719,972, entitled "Methods of Inhibiting T Cell Proliferation or IL-2 Accumulation with CTLA4-Specific Antibodies". The contents of this application are incorporated herein by reference.

GOVERNMENT FUNDING

Work described herein was supported under grants RO1CA40216 and PO1AI35225 awarded by the National Institutes of Health. The U.S. government therefore may have certain rights in this invention.

BACKGROUND OF THE INVENTION

The induction of an antigen specific T cell response requires multiple interactions between cell surface receptors on a T cell and ligands on an antigen presenting cell. The primary interaction is between the T cell receptor/CD3 complex and a major histocompatibility complex molecule, which presents an antigenic peptide to the T cell receptor, thereby triggering an antigen specific signal in the T cells. In addition to this antigen specific signal, a T cell response require a second, costimulatory signal. A costimulatory signal can be generated in a T cell by stimulation of the T cell through a cell surface receptor CD28 (Harding, F. A. (1992) *Nature* 356:607-609). Ligands for CD28 have been identified on antigen presenting cells (APCs). CD28 ligands include members of the B7 family of proteins, such as B7-1(CD80) and B7-2 (CD86) (Freedman, A. S. et al. (1987) *J. Immunol.* 137:3260-3267; Freeman, G. J. et al. (1989) *J. Immunol.* 143:2714-2722; Freeman, G. J. et al. (1991) *J. Exp. Med.* 174:625-631; Freeman, G. J. et al. (1993) *Science* 262:909-911; Azuma, M. et al. (1993) *Nature* 366:76-79; Freeman, G. J. et al. (1993) *J. Exp. Med.* 178:2185-2192). Additionally, B7-1 and B7-2 have been shown to bind another surface receptor on T cells related to CD28 termed CTLA4 (Linsley, P. S. (1991) *J. Exp. Med.* 174:561-569; Freeman, G. J. et al. (1993) *Science* 262:909-911). In contrast to CD28 which is constitutively expressed on T cells, CTLA4 is induced on T cells upon activation (Linsley, P. S. et al. (1992) *J. Exp. Med.* 176:1595-1604). Although a functional role for CTLA4 is unknown, there is some evidence that CTLA4 can synergize with CD28 in the delivery of a costimulatory signal to a T cell (Linsley, P. S. et al. (1992) *J. Exp. Med.* 176:1595-1604; Damle, N. K. et al. (1994) *J. Immunol.* 152:2686-2697).

Delivery of an antigen specific signal to a T cell in the absence of a costimulatory signal does not induce a T cell response, but rather has been found to induce a state of T cell unresponsiveness or anergy (see Schwartz, R. H. (1990) *Science* 248:1349; Jenkins, M. K. et al. (1988) *J. Immunol.* 140:3324). In a number of clinical situations it is desirable to inhibit T cell responses (e.g., in transplantation or autoimmune disorders). Thus, therapeutic approaches have been proposed to induce antigen specific T cell unresponsiveness by blocking of a costimulatory signal in T cells. For example, a CTLA4Ig fusion protein, which binds both B7-1 and B7-2, has been used to inhibit rejection of allogeneic and xenogeneic grafts (see e.g., Turka, L. A. et al. (1992) *Proc. Natl. Acad. Sci. USA* 89, 11102-11105; Lenschow, D. J. et al. (1992) *Science* 257, 789-792). Similarly, antibodies reactive with B7-1 and/or B7-2 have been used to inhibit T cell proliferation and IL-2 production in vitro and inhibit primary immune responses to antigen in vivo (Hathcock K. S. et al. (1993) *Science* 262, 905-907; Azuma, M. et al. (1993) *Nature* 366:76-79; Powers, G. D. et al. (1994) *Cell. Immunol.* 153, 298-311; Chen C. et al. (1994) *J. Immunol.* 152, 2105-2114).

An alternative approach to anergy induction for avoiding an unwanted T cell response to an antigen is to clonally delete T cells specific for the antigen, thereby eliminating the antigen specific T cells from the T cell repertoire. In vivo, T cell maturation in the thymus involves clonal deletion of potentially autoreactive T cells. Additionally, there is increasing evidence that previously activated T cells are selectively depleted in the periphery after clonal expansion and effector function has occurred (Webb, S. et al. (1990) *Cell* 63:1249-1256; Rocha, B. et al. (1991) *Science* 251:1225-1227; and Russell, J. H. et al. (1991) *Proc. Natl. Acad. Sci. USA* 88:2151-2155). Deletion, or elimination, of many types of cells, including T cells, can occur by a mechanism termed apoptosis, or programmed cell death. The occurrence of apoptosis in a cell is characterized by features including cell shrinkage, nuclear collapse and DNA fragmentation (reviewed in Cohen, J. J. et al. (1992) *Ann. Rev. Immunol.* 10:267-293). Several cell-surface molecules have been identified which, upon ligation, can induce apoptosis in a cell, including Fas and tumor necrosis factor receptors (Yonehara, S. et al. (1989) *J. Exp. Med.* 169:1747-1756; Trauth, B. C. et al. (1989) *Science* 245:301-305; Itoh, N. et al. (1991) *Cell* 66:233-239; and Greenblatt, M. S. et al. (1992) *Blood* 80:1339-1344;). However, none of these apoptotic molecules is restricted to the T cell lineage nor do they induce apoptosis in an antigen specific manner. The ability to clonally delete T cells in a manner dependent upon antigenic stimulation would provide a means for long-term inhibition of T cell responses in a variety of clinical situations without the need for chronic generalized immunosuppression of a subject with its attendant deleterious side effects.

SUMMARY OF THE INVENTION

This invention is based, at least in part, on the discovery of novel ligands which bind a T cell surface molecule and induce antigen specific apoptosis in an activated T cell. Preferably, the ligand is an antibody, or antibody fragment, which binds the T cell surface molecule CTLA4, in particular human CTLA4. Anti-CTLA4 antibodies which bind an epitope on CTLA4 that is distinct from the epitope(s) recognized by the known CTLA4 ligands B7-1 and B7-2 are particularly preferred for use in inducing antigen specific T cell apoptosis. The antibodies can be polyclonal or monoclonal antibodies, or fragments thereof. Chimeric and humanized monoclonal antibodies, and fragments thereof, are encompassed by the invention. In another embodiment, the ligand is a soluble recombinant form of a novel CTLA4 ligand distinct from B7-1 and B7-2 that can induce T cell apoptosis. Alternatively, the ligand can be a modified form of B7-1 or B7-2 that binds CTLA4 without binding CD28 (e.g., the modified form of B7-1 or B7-2 binds the same epitope on CTLA4 recognized by the antibodies of the invention and induces apoptosis in a T cell).

Another embodiment of the invention pertains to ligands which bind an epitope on CTLA4 which is distinct from an epitope bound by the known B7-1 and B7-2 ligands and which induces apoptosis in a T cell. Preferably, the CTLA4 epitope recognized by a ligand, e.g., antibody, of the invention includes or encompasses an amino acid sequence:

(Xaa)$_n$-Leu-Thr-Phe-Leu-Asp-Asp-(Xaa)$_n$ (SEQ ID NO: 33), wherein Xaa is any amino acids and n=0-20, preferably 0-5, more preferably 0-3. This CTLA4 epitope is found in human CTLA4 at amino acid positions 59 to 64. Thus, typically, Xaa are additional amino acid residues found at either the amino or carboxy side, or both the amino and carboxy sides, of the epitope in the human CTLA4 amino acid sequence (SEQ ID NO: 36). Alternatively, Xaa can be an amino acid residue which increases the solubility of the resulting peptide or enhances the immunogenicity of the resulting peptide for use as an immunogen. For example, Xaa can be a charged amino acid (e.g., lysine, arginine) which may be added to increase the solubility of the peptide. Alternatively, Xaa can be cysteines added to increase dimerization of the resulting peptide.

The ligands of the invention, when combined with a pharmaceutically acceptable carrier, can be used in compositions suitable for pharmaceutical administration.

The ligands of the invention are useful for clonally deleting activated T cells in an antigen specific manner, either in vitro or in vivo, by induction of T cell apoptosis. In one embodiment, an activated T cell is contacted in vitro with a first agent that stimulates the T cell through the TCR/CD3 complex and a second agent which crosslinks an epitope on CTLA4, or provides an intracellular signal through a CTLA4-mediated pathway, that induces apoptosis in the T cell. Alternatively, the second agent is administered to a subject, together with a pharmaceutically acceptable carrier, to induce T cell apoptosis in vivo in the subject. A preferred second agent is an anti-CTLA4 antibody of the invention. In addition to inducing apoptosis through a CTLA4-mediated pathway, one or more additional agents can be administered to a subject to inhibit delivery of stimulatory signals to T cells. For example, an agent which inhibits the production or function of a T cell growth factor(s) in the subject, such as an anti-IL-2 receptor antibody, an anti-IL-2 antibody or cyclosporin A, may also be administered to the subject. Alternatively or additionally, another agent which inhibits delivery of a costimulatory signal to T cells, such as a molecule (e.g., antibody or soluble fusion protein) which inhibits an interaction between CD28 and B7-1 and/or B7-2, may also be administered in conjunction with an agent which induces T cell apoptosis.

Clonal deletion of T cells by induction of apoptosis in accordance with the methods described herein is applicable to a variety of clinical situations. For example, alloreactive T cells can be deleted from a transplant recipient to inhibit rejection of transplanted cells, tissues or organs. Additionally, alloreactive T cells can be deleted from donor bone marrow prior to bone marrow transplantation to inhibit graft versus host disease in a transplant recipient. In other applications, autoreactive T cells are deleted to treat autoimmune disorders and allergen-specific T cells are deleted to treat allergies. Virally-infected or malignant T cells which express CTLA4 on their surface can also be eliminated according to the methods of the invention.

In addition to providing for induction of apoptosis in T cells, the invention also provides methods for inhibiting T cell apoptosis. In one embodiment, T cell apoptosis is inhibited by interfering with an interaction between CTLA4 on a T cell and a CTLA4 ligand that induces apoptosis on an antigen presenting cell. A blocking form of a CTLA4 antibody or fragment thereof (e.g., Fab fragment) or a blocking soluble form of the CTLA4 ligand can be used to inhibit T cell apoptosis. Alternatively, an agent which acts intracellularly to inhibit apoptosis in a T cell through a CTLA4-mediated pathway can be used. The methods for inhibiting apoptosis are useful for enhancing T cell responses, such as against tumor cells and pathogens (e.g., bacteria, viruses, fungi, parasites and the like) and for enhancing the efficacy of vaccination.

DETAILED DESCRIPTION OF THE INVENTION

Figure 1A:
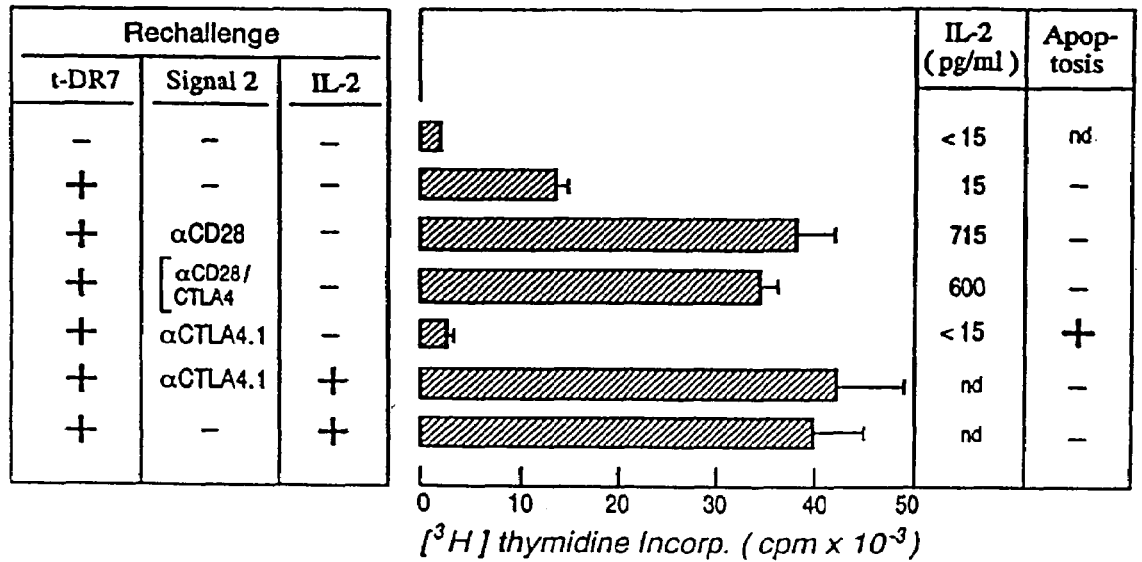
FIG. 1A is a graphic representation of T cell responses (proliferation, IL-2 production or apoptosis) by activated DR7-specific T cell clones upon rechallenge with antigen (t-DR7) and the indicated second signals, demonstrating induction of apoptosis by an anti-CTLA4 monoclonal antibody (mAb).
Figure 1B:
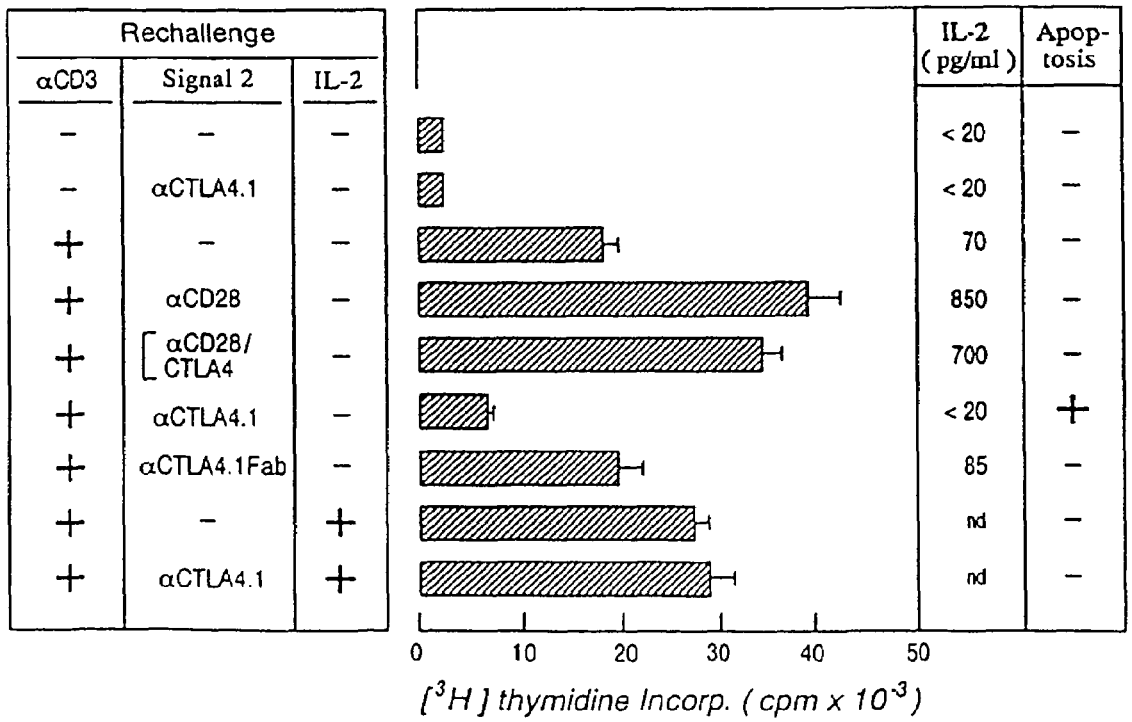
FIG. 1B is a graphic representation of T cell responses (proliferation, IL-2 production or apoptosis) by normal peripheral blood CD4$^+$T cell blasts upon rechallenge with anti-CD3 and the indicated second signals, demonstrating induction of apoptosis by an anti-CTLA4 mAb.

The current invention is based, at least in part, on the discovery that crosslinking of a T cell surface molecule, such as CTLA4, on an activated T cell, together with delivery of a signal to the activated T cell through the TCR/CD3 complex, induces apoptosis in the T cell. When antigen is used to deliver the signal through the TCR/CD3 complex, the result is antigen specific apoptosis. Accordingly, the invention provides a means to clonally delete activated T cells in an antigen specific manner.

One aspect of the invention provides novel isolated ligands which bind a molecule present on the surface of a T cell and induce apoptosis in activated T cells. As used herein, a "ligand" is a molecule which displays specific reactivity for (i.e., specifically recognizes and binds to) a target molecule. The ligands of the invention bind a T cell specific surface molecule to trigger an apoptotic signal in the T cell. A surface molecule that is "T cell specific" is exclusively or preferentially (i.e., predominantly) expressed on T lymphocytes compared to other cell types. A preferred T cell surface molecule to which a ligand of the invention binds is CTLA4. In one embodiment, CTLA4 designates a human protein having an amino acid sequence as shown in SEQ ID NO: 36 (see also Harper, K. et al. (1991) *J. Immunol.* 147:1037-1044) and encoded by a cDNA having a nucleotide sequence as shown in SEQ ID NO: 35 (see also Dariavach, F. et al. (1988) *Eur. J. Immunol.* 18:1901-1905). In another embodiment, CTLA4 designates a homolog of the human protein from another mammalian species, such as mouse CTLA4 (a cDNA encoding mouse CTLA4 is described in Brunet, J-F. et al. (1987) *Nature* 328:267-270). Additionally, ligands which bind proteins structurally related to CTLA4 (e.g., having a homologous amino acid sequence) that display T cell specific expression and are capable of mediating antigen specific apoptosis in T cells are contemplated by the invention.

The ligands of the invention are capable of inducing apoptosis, or an apoptotic signal, in activated T cells in an antigen specific manner. The term "apoptosis" is intended to describe a cellular process of programmed cell death characterized by the presence of cell shrinkage, nuclear collapse, and, most typically, cellular DNA fragmentation. "Antigen specific" apoptosis is intended to mean that, within a population of T cells, apoptosis occurs only in those T cells having specificity for a particular antigen, such as an alloantigen or an autoantigen. Antigen specific apoptosis is achieved by stimulating an activated T cell both with antigen and a CTLA4 ligand of the invention. Alternatively, non-antigen specific (i.e., polyclonal) apoptosis can be achieved by delivering a non-antigen specific signal to the T cell through the TCR/CD3 complex, for example with an anti-CD3 antibody, together with a CTLA4 ligand of the invention. Apoptosis is induced in an "activated" T cell which expresses CTLA4 on its surface. A T cell can be activated to express CTLA4 in an antigen specific manner, e.g., by stimulating the T cell with antigen together with a costimulatory signal (e.g., signaling through the CD28 pathway). Alternatively, T cells may be polyclonally activated, for example by culture with a mitogen such as phytohemagglutinin (PHA) or a phorbol ester such as phorbol myristic acetate (PMA).

In a preferred embodiment, a ligand of the invention is an antibody which binds to CTLA4 (also referred to herein as an anti-CTLA4 antibody). The term "antibody" as used herein refers to immunoglobulin molecules and immunologically active portions of immunoglobulin molecules, i.e., molecules that contain an antigen binding site which specifically binds (immunoreacts with) an antigen, such as CTLA4. Structurally, the simplest naturally occurring antibody (e.g., IgG) comprises four polypeptide chains, two heavy (H) chains and two light (L) chains inter-connected by disulfide bonds. It has been shown that the antigen-binding function of an antibody can be performed by fragments of a naturally-occurring antibody. Thus, these antigen-binding fragments are also intended to be designated by the term "antibody". Examples of binding fragments encompassed within the term antibody include (i) an Fab fragment consisting of the VL, VH, CL and CH1 domains; (ii) an Fd fragment consisting of the VH and CH1 domains; (iii) an Fv fragment consisting of the VL and VH domains of a single arm of an antibody, (iv) a dAb fragment (Ward et al., (1989) Nature 341:544-546) which consists of a VH domain; (v) an isolated complimentarity determining region (CDR); and (vi) an F(ab')$_2$ fragment, a bivalent fragment comprising two Fab fragments linked by a disulfide bridge at the hinge region. Furthermore, although the two domains of the Fv fragment are coded for by separate genes, a synthetic linker can be made that enables them to be made as a single protein chain (known as single chain Fv (scFv); Bird et al. (1988) Science 242:423-426; and Huston et al. (1988) PNAS 85:5879-5883) by recombinant methods. Such single chain antibodies are also encompassed within the term "antibody". Preferred antibody fragments for inducing apoptosis are those which are capable of crosslinking their target antigen, e.g., bivalent fragments such as F(ab')$_2$ fragments. Alternatively, an antibody fragment which does not itself crosslink its target antigen (e.g., a Fab fragment) can be used in conjunction with a secondary antibody which serves to crosslink the antibody fragment, thereby crosslinking the target antigen. Additionally, a noncrosslinking antibody fragment (e.g., an Fab fragment) can be used to block or inhibit apoptosis as described below. Antibodies can be fragmented using conventional techniques as described herein and the fragments screened for utility in the same manner as described for whole antibodies. An antibody of the invention is further intended to include bispecific and chimeric molecules having a CTLA4 binding portion.

The language "a desired binding specificity for a CTLA4 epitope", as well as the more general language "an antigen binding site which specifically binds (immunoreacts with)", refers to the ability of individual antibodies to specifically immunoreact with a T cell surface molecule, e.g. CTLA4. That is, it refers to a non-random binding reaction between an antibody molecule and an antigenic determinant of CTLA4. The desired binding specificity is typically determined from the reference point of the ability of the antibody to differentially bind a CTLA4 antigen and an unrelated antigen, and therefore distinguish between two different antigens, particularly where the two antigens have unique epitopes. An antibody which binds specifically to a CTLA4 epitope is referred to as a "specific antibody".

"Antibody combining site", as used herein, refers to that structural portion of an antibody molecule comprised of a heavy and light chain variable and hypervariable regions that specifically binds (immunoreacts with) antigen. The term "immunoreact" or "reactive with" in its various forms is used herein to refer to binding between an antigenic determinant-containing molecule and a molecule containing an antibody combining site such as a whole antibody molecule or a portion thereof.

The term "epitope", as used herein, refers to the actual structural portion of the antigen that is immunologically bound by an antibody combining site. The term is also used interchangeably with "antigenic determinant". A ligand, e.g., antibody, of the invention preferably binds to an epitope on CTLA4 which is distinct from (i.e., different than) an epitope(s) bound by B7-1 or B7-2. That is, the CTLA4 ligand binds to a site on CTLA4 which is distinct from the B7-1 or B7-2 binding site on CTLA4. The binding of a CTLA4 ligand to a CTLA4 epitope distinct from the B7-1 or B7-2 binding site is indicated by the inability of the ligand to inhibit binding of B7-1 or B7-2 to CTLA4 or vice versa (i.e., the inability of B7-1 or B7-2 to inhibit binding of the CTLA4 ligand to CTLA4). This can be assessed, for example, using an enzyme linked immunosorbent assay (ELISA) and soluble B7-1, B7-2 and CTLA4 fusion proteins as described in Example 2. Preferably, a Fab fragment is used to assess the ability of an antibody to inhibit binding of B7-1 or B7-2 to CTLA4 to reduce nonspecific inhibition due to steric hindrance.

A preferred human CTLA4 epitope to which a CTLA4 ligand of the invention binds includes or encompasses, an amino acid sequence:

(Xaa)$_n$-Leu-Thr-Phe-Leu-Asp-Asp-(Xaa)$_n$ (SEQ ID NO: 33), wherein Xaa is any amino acid and n=0-20, more preferably 0-10, even more preferably 0-5, most preferably 0-3. In native human CTLA4, this sequence is located in the extracellular domain in the complimentary determining region 2 (CDR2)-like region at amino acid positions 59 to 64 of SEQ ID NO: 36. Thus, typically, Xaa are additional amino acid residues found at either the amino or carboxy side, or both the amino and carboxy sides, of the core epitope in the human CTLA4 (the full-length amino acid sequence of which is shown in SEQ ID NO: 36). It will be appreciated by those skilled in the art that in the native protein, additional non-contiguous amino acid residues may also contribute to the conformational epitope recognized by the antibody. Synthetic peptides encompassing the epitope can be created which includes other amino acid residues flanking the core six amino acid residues (i.e., Xaa can alternatively be other amino acid residues than those found in the native CTLA4 protein). These flanking amino acids can function to alter the properties of the resulting peptide, for example to increase the solubility, enhance the immunogenicity or promote dimerization of the resultant peptide. When the peptide is to be used as an immunogen, one or more charged amino acids (e.g., lysine, arginine) can be included to increase the solubility of the peptide and/or enhance the immunogenicity of the peptide. Alternatively, cysteine residues can be included to increase the dimerization of the resulting peptide.

These and other embodiments of the invention are described in further detail in the following subsections:

I. CTLA4 and Anti-CTLA4 Antibodies

The CTLA4 antigen is a member of a family of T cell surface molecules that can bind costimulatory molecules found on the surface of B lymphocytes, professional antigen presenting cells (e.g., monocytes, dendritic cells, Langerhan cells) and others cells (e.g., keratinocytes, endothelial cells, astrocytes, fibroblasts, oligodendrocytes) which present antigen to immune cells. Another member of this family is the T cell surface molecule CD28, which shares 31% overall amino acid identity with CTLA4 (Harper, K. et al. (1991) *J. Immunol.* 147:1037-1044). The CD28 and CTLA4 molecules each bind costimulatory molecules such B7-1 and B7-2. However, the observation that an anti-CD28 Fab fragment completely inhibits T cell responses to costimulation by both B7-1 and B7-2 supports the hypothesis that B7 family costimulation is predominantly mediated via CD28 (see Gimmi, C. D. et al. (1991) *Proc. Natl. Acad. Sci. USA* 88:6575-6579; and Freeman, G. J. et al. (1993) *J. Exp. Med.* 178:2185-2192). In contrast, it has now been discovered that T cell apoptosis can be mediated via CTLA4 by interaction with a novel CTLA4 ligand.

The CTLA4 molecule is not expressed on resting T cells but is induced upon activation. For example, after stimulation of normal resting human T cells with PHA or PMA for 24 hours, CTLA4 mRNA is expressed in both the CD4$^+$ and CD8$^+$ subsets (see Freeman, G. J. et al. (1992) *J. Immunol.* 149:3795-3801). Furthermore, CTLA4 expression has been observed on HTLV-I and HIV infected T cell lines (see Freeman, G. J. et al. (1992) *J. Immunol.* 149:3795-3801; Haffar, O. K. et al. (1993) *Proc. Natl. Acad. Sci. USA* 90:11094-11098).

Purification techniques for T cell surface molecules, such as CTLA4, have been established, and, additionally, CTLA4 genes and cDNA have been cloned from both human and mouse (see, for example, Dariavach, F. et al. (1988) *Eur. J. Immunol.* 18:1901-1905; and Brunet, J-F. et al. (1987) *Nature* 328:267-270). The nucleotide sequence and deduced amino acid sequence of human CTLA4 are shown in SEQ ID NO: 35 and 36, respectively. A CTLA4 protein, or peptide thereof, can be obtained by purification of the natural protein or by recombinant expression. A modified recombinant form of CTLA4, such as a CTLA4 extracellular domain, can be expressed by incorporating a CTLA4-encoding DNA into an expression vector and introduced the vector into a host cell, either a prokaryotic or eukaryotic cell. For example, a CTLA4 extracellular domain, or peptide thereof, can be expressed in bacterial cells such as *E. coli*, insect cells (e.g., using a baculovirus expression system), yeast, or mammalian cells such as Chinese hamster ovary cells (CHO), COS or NS0 cells. Other suitable host cells and expression vectors may be found in Goeddel, (1990) supra or are known to those skilled in the art.

Examples of vectors for expression in yeast *S. cerivisae* include pYepSec1 (Baldari. et al., (1987) *Embo J.* 6:229-234), pMFa (Kurjan and Herskowitz, (1982) *Cell* 30:933-943), pJRY88 (Schultz et al., (1987) *Gene* 54:113-123), and pYES2 (Invitrogen Corporation, San Diego, Calif.). Baculovirus vectors available for expression of proteins in cultured insect cells (SF 9 cells) include the pAc series (Smith et al., (1983) *Mol. Cell Biol.* 3:2156-2165) and the pVL series (Lucklow, V. A., and Summers, M. D., (1989) *Virology* 170: 31-39). Generally, COS cells (Gluzman, Y., (1981) *Cell* 23:175-182) are used in conjunction with such vectors as pCDM8 (Seed, B., (1987) *Nature* 329:840) for transient amplification/expression in mammalian cells, while CHO (dhfr$^-$ Chinese Hamster Ovary) cells are used with vectors such as pMT2PC (Kaufman et al. (1987), *EMBO J.* 6:187-195) for stable amplification/expression in mammalian cells. Recombinant proteins can be produced in the NS0 myeloma cell line (available from the ECACC; catalog #85110503) as described in Galfre, G. and Milstein, C. ((1981) *Methods in Enzymology* 73(13):3-46; and *Preparation of Monoclonal Antibodies: Strategies and Procedures*, Academic Press, N.Y., N.Y.).

Alternatively, a recombinant extracellular portion of CTLA4 can be expressed in bacterial cells, such as *E. coli*. Preferred *E. coli* expression systems include the inducible expression vectors pTrc (Amann et al., (1988) *Gene* 69:301-315) and the pET 11 (Studier et al., *Gene Expression Technology: Methods in Enzymology* 185, Academic Press, San Diego, Calif. (1990) 60-89; commercially available from Novagen). In the pTrc vector system, the inserted gene is expressed with a pelB signal sequence by host RNA polymerase transcription from a hybrid trp-lac fusion promoter. After induction, recombinant CTLA4 can be purified from the periplasmic fraction. In the pET 11 vector system, the target gene is expressed as non-fusion protein by transcription from the T7 gn10-lac 0 fusion promoter mediated by a coexpressed viral RNA polymerase (T7 gn1). This viral polymerase is supplied by host *E. coli* strains BL21 (DE3) or HMS174(DE3) from a resident λ prophage harboring a T7 gn1 under the transcriptional control of the lacUV 5 promoter. In this system, recombinant CTLA4 can be purified from inclusion bodies in a denatured form and, if desired, renatured by step gradient dialysis to remove denaturants. Expression of the extracellular domain of human CTLA4 in *E. coli* is described in further detail in Example 6.

A recombinant cell-surface form of CTLA4 can be expressed on a mammalian cell by modification of the transmembrane and/or cytoplasmic portion of the protein (the native full-length form of the protein is not expressed efficiently on the surface of many mammalian cells). For example, the transmembrane and cytoplasmic domains can be replaced by an alternative structure for tethering the molecule to the cell surface, such as a glycophosphatidylinositol (gpi) anchor (as described in Example 1) or fatty acid anchor. Alternatively, cell-surface expression of CTLA4 can be achieved using a heterologous transmembrane domain or by deleting the cytoplasmic domain. CTLA4 can also be expressed in mammalian cells as a soluble fusion protein (e.g., an immunoglobulin fusion protein) as described in Linsley, P. S. et al. (1991) *J. Exp. Med.* 174:561-569.

For expression in mammalian cells, vector DNA is introduced into mammalian cells via conventional techniques such as calcium phosphate or calcium chloride co-precipitation, DEAE-dextran-mediated transfection, lipofectin, or electroporation. Suitable methods for transforming host cells can be found in Sambrook et al. (*Molecular Cloning: A Laboratory Manual*, 2nd Edition, Cold Spring Harbor Laboratory press (1989)), and other laboratory textbooks. When used in mammalian cells, the expression vector's control functions are often provided by viral genetic material. For example, commonly used promoters are derived from polyoma, Adenovirus 2, cytomegalovirus and most frequently, Simian Virus 40.

CTLA4 proteins, or peptides thereof, expressed in mammalian cells or elsewhere, can be purified according to standard procedures of the art, including ammonium sulfate precipitation, fractionation column chromatography (e.g. ion exchange, gel filtration, electrophoresis, affinity chromatography, etc.) and ultimately, crystallization (see generally, "Enzyme Purification and Related Techniques", *Methods in Enzymology*, 22:233-577 (1971)).

Anti-CTLA4 antibodies can be generated by those skilled in the art by following standard techniques. For instance, CTLA4 molecules from a variety of species, whether in soluble form or membrane bound, can be used to induce the formation of anti-CTLA4 antibodies. Such antibodies may either be polyclonal or monoclonal antibodies, or antigen binding fragments of such antibodies. Of particular significance for use in therapeutic applications are antibodies that crosslink an epitope on CTLA4 that induces T cell apoptosis. Alternatively, antibodies, or fragments thereof (e.g., Fab) fragments, that specifically bind this "apoptotic epitope) but which do not crosslink CTLA4 or induce apoptosis can be used therapeutically to inhibit T cell apoptosis. The invention encompasses antibodies which bind to human CTLA4 (e.g., an anti-human CTLA4 mAb, preferably a human or humanized mAb), as well as antibodies which bind to CTLA4 proteins in other species, e.g., monkeys, cattle, horses, goats, sheep, dogs, cats, rats, mice, etc., which can be used for veterinary purposes. Methodologies for generating anti-CTLA4 antibodies are described in further detail below:

A. The Immunogen. The term "immunogen" is used herein to describe a composition containing a CTLA4 peptide or protein as an active ingredient used for the preparation of antibodies against CTLA4. When a CTLA4 peptide or protein is used to induce antibodies it is to be understood that the peptide can be used alone, or linked to a carrier as a conjugate, or as a peptide polymer.

To generate suitable anti-CTLA4 antibodies, the immunogen should contain an effective, immunogenic amount of a CTLA4 peptide or protein, optionally as a conjugate linked to a carrier. The effective amount of peptide per unit dose depends, among other things, on the species of animal inoculated, the body weight of the animal and the chosen immunization regimen as is well known in the art. The immunogen preparation will typically contain peptide concentrations of about 10 micrograms to about 500 milligrams per immunization dose, preferably about 50 micrograms to about 50 milligrams per dose. An immunization preparation can also include an adjuvant as part of the diluent. Adjuvants such as complete Freund's adjuvant (CFA), incomplete Freund's adjuvant (IFA) and alum are materials well known in the art, and are available commercially from several sources.

Those skilled in the art will appreciate that, instead of using natural occurring forms of CTLA4 for immunization, synthetic peptides can alternatively be employed towards which antibodies can be raised for use in this invention. Both soluble and membrane bound CTLA4 protein or peptide fragments are suitable for use as an immunogen and can also be isolated by immunoaffinity purification as well. A purified form of CTLA4 protein, such as may be isolated as described above or as known in the art, can itself be directly used as an immunogen, or alternatively, can be linked to a suitable carrier protein by conventional techniques, including by chemical coupling means as well as by genetic engineering using a cloned gene of the CTLA4 protein. The purified CTLA4 protein can also be covalently or noncovalently modified with non-proteinaceous materials such as lipids or carbohydrates to enhance immunogenecity or solubility. Alternatively, a purified CTLA4 protein can be coupled with or incorporated into a viral particle, a replicating virus, or other microorganism in order to enhance immunogenicity. The CTLA4 protein may be, for example, chemically attached to the viral particle or microorganism or an immunogenic portion thereof.

In an illustrative embodiment, a purified CTLA4 protein, or a peptide fragment thereof (e.g., produced by limited proteolysis or recombinant DNA techniques) is conjugated to a carrier which is immunogenic in animals. Preferred carriers include proteins such as albumins, serum proteins (e.g., globulins and lipoproteins), and polyamino acids. Examples of useful proteins include bovine serum albumin, rabbit serum albumin, thyroglobulin, keyhole limpet hemocyanin, egg ovalbumin and bovine gamma-globulins. Synthetic polyamino acids such as polylysine or polyarginine are also useful carriers. With respect to the covalent attachment of CTLA4 protein or peptide fragments to a suitable immunogenic carrier, there are a number of chemical cross-linking agents that are known to those skilled in the art. Preferred cross-linking agents are heterobifunctional cross-linkers, which can be used to link proteins in a stepwise manner. A wide variety of heterobifunctional cross-linkers are known in the art, including succinimidyl 4-(N-maleimidomethyl) cyclohexane-1-carboxylate (SMCC), m-Maleimidobenzoyl-N-hydroxysuccinimide ester (MBS); N-succinimidyl (4-iodoacetyl) aminobenzoate (SIAB), succinimidyl 4-(p-maleimidophenyl) butyrate (SMPB), 1-ethyl-3-(3-dimethylaminopropyl) carbodiimide hydrochloride (EDC); 4-succinimidyl-oxycarbonyl-a-methyl-a-(2-pyridyldithio)-tolune (SMPT), N-succinimidyl 3-(2-pyridyldithio) propionate (SPDP), succinimidyl 6-[3-(2-pyridyldithio) propionate] hexanoate (LC-SPDP).

In may also be desirable to simply immunize an animal with whole cells which express a CTLA4 protein on their surface. Various cell lines can be used as immunogens to generate monoclonal antibodies to a CTLA4 antigen, including, but not limited to activated T cells. For example, peripheral blood T cells obtained from a subject can be activated in vitro with anti-CD3 antibodies, PHA or PMA. Alternatively, an antigen specific (e.g., alloreactive) T cell clone can be activated to express CTLA4 by presentation of antigen, together with a costimulatory signal, to the T cell. Whole cells that can be used as immunogens to produce CTLA4 specific antibodies also include recombinant transfectants. For example, COS and CHO cells can be reconstituted by transfection with a CTLA4-gpi cDNA, as described in Example 1, to produce cells expressing CTLA4 on their surface. These transfectant cells can then be used as immunogens to produce anti-CTLA4 antibodies. Other examples of transfectant cells are known, particularly eukaryotic cells able to glycosylate the CTLA4 protein, but any procedure that works to express transfected CTLA4 genes on the cell surface could be used to produce the whole cell immunogen.

Alternative to a CTLA4-expressing cell or an isolated CTLA4 protein, peptide fragments of CTLA4 can be used as immunogens to generate anti-CTLA4 antibodies. In a preferred embodiment, the CTLA4 epitope bound by the antibody comprises an amino acid sequence: $(Xaa)_n$-Leu-Thr-Phe-Leu-Asp-Asp-$(Xaa)_n$ (SEQ ID NO: 33), wherein Xaa is any amino acid and n=0-20, preferably 0-10, more preferably 0-5, most preferably 0-3. Thus, a peptide having the amino acid sequence of SEQ ID NO: 33 can be used as an immunogen. Accordingly, the invention further encompasses an isolated CTLA4 peptide comprising an amino acid sequence: (Xaa)$_n$-Leu-Thr-Phe-Leu-Asp-Asp-(Xaa)$_n$ (SEQ ID NO: 33), wherein Xaa is any amino acid and n=0-20.

Alternatively, it has been found that anti-CTLA4 antibodies capable of inducing apoptosis can cross-react with a number of other peptide sequences (determined by phage display technology as described in Example 3). Examples of these other peptide sequences are shown below:

| | |
|---|---|
| GGLVMIERFNKLE[LTWADD]D | (SEQ ID NO: 15) |
| VCALPDVGYEF[LTSNAD]EPC | (SEQ ID NO: 16) |
| YLANHFGWTS[MVWDAD]DTGH | (SEQ ID NO: 17) |
| RNWARRTSN[LSWDGD]DGSRG | (SEQ ID NO: 18) |
| TAERCVS[LTWNDD]TCDLTGA | (SEQ ID NO: 19) |
| FGLQS[LCWEED]AGLVFGQDS | (SEQ ID NO: 20) |
| NKES[LNWADE]LVRKDPPHGV | (SEQ ID NO: 21) |
| YTE[LTFAND]GLGSGKNLIPK | (SEQ ID NO: 22) |
| YGA[LTCFND]RSDCFFTSPFI | (SEQ ID NO: 23) |
| QS[LTFEDD]GSSFLIYRATSD | (SEQ ID NO: 24) |
| H[LNWGEE]VRHQGEPRADQPF | (SEQ ID NO: 25) |
| V[LTFLER]LLPAVVPRSCHPG | (SEQ ID NO: 26) |
| [LSWGLE]PWEGSFLWLTESPM | (SEQ ID NO: 27) |
| [LNWDID]SMPMGVYCDVPDSC | (SEQ ID NO: 28) |

Any of these peptides, or other peptides containing a stretch of six amino acids bracketed in bold type (representing the epitope bound by the antibody) possibly flanked by alternative amino acid residues, can also be used as immunogens to produce an anti-CTLA4 antibody of the invention and are encompassed by the invention. For use as immunogens, peptides can be modified to increase solubility and/or enhance immunogenicity as described above.

As an alternative to use of a protein or peptide as an immunogen, it is possible to use nucleic acid (e.g., DNA) encoding the protein or peptide as an immunogen for so-called genetic immunization. Thus, the term "immunogen" is also intended to include nucleic acid encoding a protein or peptide against which antibodies are to be raised. To raise antibodies by genetic immunization, an expression vector construct containing nucleic acid encoding the protein of interest (e.g, CTLA4 or a peptide thereof) is delivered intracellularly into the skin of an animal (e.g., mouse) by coating particles (e.g., gold particles) with the construct and injecting the particles into the skin. This results in antigen production in the skin and development of a specific antibody response (see e.g., Tang, D. C. et al. (1992) *Nature* 356:152-154; Eisenbraun, M. D. et al. (1993) *DNA Cell Biol.* 12:791-797; Wang, B. et al. (1993) *DNA Cell Biol.* 12:799-805).

B. Polyclonal anti-CTLA4 Antibodies. Polyclonal antibodies to a purified CTLA4 protein or peptide fragment thereof can generally be raised in animals by multiple subcutaneous (sc) or intraperitoneal (ip) injections of a CTLA4 immunogen, such as the extracellular domain of the CTLA4 protein, and an adjuvant. A polyclonal anti-CTLA4 antisera can be produced, for example, as described in Lindsten, T. et al. (1993) *J. Immunol.* 151:3489-3499. In an illustrative embodiment, animals are typically immunized against the immunogenic CTLA4 protein, peptide or derivative by combining about 1 µg to 1 mg of protein with Freund's complete adjuvant and injecting the solution intradermally at multiple sites. One month later the animals are boosted with ⅕ to ⅒ the original amount of immunogen in Freund's complete adjuvant (or other suitable adjuvant) by subcutaneous injection at multiple sites. Seven to 14 days later, the animals are bled and the serum is assayed for anti-CTLA4 titer (e.g., by ELISA). Animals are boosted until the titer plateaus. Also, aggregating agents such as alum can be used to enhance the immune response.

Such mammallian-produced populations of antibody molecules are referred to as "polyclonal" because the population comprises antibodies with differing immunospecificities and affinities for CTLA4. The antibody molecules are then collected from the mammal (e.g., from the blood) and isolated by well known techniques, such as protein A chromatography, to obtain the IgG fraction. To enhance the specificity of the antibody, the antibodies may be purified by immunoaffinity chromatography using solid phase-affixed immunogen. The antibody is contacted with the solid phase-affixed immunogen for a period of time sufficient for the immunogen to immunoreact with the antibody molecules to form a solid phase-affixed immunocomplex. The bound antibodies are separated from the complex by standard techniques.

C. Monoclonal anti-CTLA4 Antibodies. The term "monoclonal antibody" or "monoclonal antibody composition", as used herein, refers to a population of antibody molecules that contain only one species of an antigen binding site capable of immunoreacting with a particular epitope of a CTLA4 antigen. A monoclonal antibody composition thus typically displays a single binding affinity for a particular CTLA4 protein with which it immunoreacts. Preferably, the monoclonal antibody used in the subject method is further characterized as immunoreacting with a CTLA4 derived from humans.

Monoclonal antibodies useful in the compositions and methods of the invention are directed to an epitope of a CTLA4 antigen on activated T cells, such that complex formation between the antibody and the CTLA4 antigen (also referred to herein as ligation) induces apoptosis in the activated T cell. A monoclonal antibody to an epitope of CTLA4 can be prepared by using a technique which provides for the production of antibody molecules by continuous cell lines in culture. These include but are not limited to the hybridoma technique originally described by Kohler and Milstein (1975, *Nature* 256:495-497), and the more recent human B cell hybridoma technique (Kozbor et al. (1983) *Immunol Today* 4:72), EBV-hybridoma technique (Cole et al. (1985), *Monoclonal Antibodies and Cancer Therapy*, Alan R. Liss, Inc., pp. 77-96), and trioma techniques. Other methods which can effectively yield monoclonal antibodies useful in the present invention include phage display techniques (Marks et al. (1992) *J Biol Chem* 16007-16010).

In one embodiment, the antibody preparation applied in the subject method is a monoclonal antibody produced by a hybridoma cell line. Hybridoma fusion techniques were first introduced by Kohler and Milstein (Kohler et al. *Nature* (1975) 256:495-97; Brown et al. (1981) *J. Immunol* 127:539-46; Brown et al. (1980) *J Biol Chem* 255:4980-83; Yeh et al. (1976) *PNAS* 76:2927-31; and Yeh et al. (1982) *Int. J. Cancer* 29:269-75). Thus, the monoclonal antibody compositions of the present invention can be produced by the following method, which comprises the steps of:

(a) Immunizing an animal with a CTLA4 protein or peptide thereof. The immunization is typically accomplished by administering the CTLA4 immunogen to an immunologically competent mammal in an immunologically effective amount, i.e., an amount sufficient to produce an immune response. Preferably, the mammal is a rodent such as a rabbit, rat or mouse. The mammal is then maintained for a time period sufficient for the mammal to produce cells secreting antibody molecules that immunoreact with the CTLA4 immunogen. Such immunoreaction is detected by screening the antibody molecules so produced for immunoreactivity with a preparation of the immunogen protein. Optionally, it may be desired to screen the antibody molecules with a preparation of the protein in the form in which it is to be detected by the antibody molecules in an assay, e.g., a membrane-associated form of CTLA4. These screening methods are well known to those of skill in the art, e.g., enzyme-linked immunosorbent assay (ELISA) and/or flow cytometry.

(b) A suspension of antibody-producing cells removed from each immunized mammal secreting the desired antibody is then prepared. After a sufficient time, the mouse is sacrificed and somatic antibody-producing lymphocytes are obtained. Antibody-producing cells may be derived from the lymph nodes, spleens and peripheral blood of primed animals. Spleen cells are preferred, and can be mechanically separated into individual cells in a physiologically tolerable medium using methods well known in the art. Mouse lymphocytes give a higher percentage of stable fusions with the mouse myelomas described below. Rat, rabbit and frog somatic cells can also be used. The spleen cell chromosomes encoding desired immunoglobulins are immortalized by fusing the spleen cells with myeloma cells, generally in the presence of a fusing agent such as polyethylene glycol (PEG). Any of a number of myeloma cell lines may be used as a fusion partner according to standard techniques; for example, the P3-NS1/1-Ag4-1, P3-x63-Ag8.653 or Sp2/O-Ag14 myeloma lines. These myeloma lines are available from the American Type Culture Collection (ATCC), Rockville, Md.

The resulting cells, which include the desired hybridomas, are then grown in a selective medium, such as HAT medium, in which unfused parental myeloma or lymphocyte cells eventually die. Only the hybridoma cells survive and can be grown under limiting dilution conditions to obtain isolated clones. The supernatants of the hybridomas are screened for the presence of antibody of the desired specificity, e.g., by immunoassay techniques using the antigen that has been used for immunization. Positive clones can then be subcloned under limiting dilution conditions and the monoclonal antibody produced can be isolated. Various conventional methods exist for isolation and purification of the monoclonal antibodies so as to free them from other proteins and other contaminants. Commonly used methods for purifying monoclonal antibodies include ammonium sulfate precipitation, ion exchange chromatography, and affinity chromatography (see, e.g., Zola et al. in *Monoclonal Hybridoma Antibodies: Techniques And Applications*, Hurell (ed.) pp. 51-52 (CRC Press 1982)). Hybridomas produced according to these methods can be propagated in vitro or in vivo (in ascites fluid) using techniques known in the art.

Generally, the individual cell line may be propagated in vitro, for example in laboratory culture vessels, and the culture medium containing high concentrations of a single specific monoclonal antibody can be harvested by decantation, filtration or centrifugation. Alternatively, the yield of monoclonal antibody can be enhanced by injecting a sample of the hybridoma into a histocompatible animal of the type used to provide the somatic and myeloma cells for the original fusion. Tumors secreting the specific monoclonal antibody produced by the fused cell hybrid develop in the injected animal. The body fluids of the animal, such as ascites fluid or serum, provide monoclonal antibodies in high concentrations. When human hybridomas or EBV-hybridomas are used, it is necessary to avoid rejection of the xenograft injected into animals such as mice. Immunodeficient or nude mice may be used or the hybridoma may be passaged first into irradiated nude mice as a solid subcutaneous tumor, cultured in vitro and then injected intraperitoneally into pristane primed, irradiated nude mice which develop ascites tumors secreting large amounts of specific human monoclonal antibodies.

Media and animals useful for the preparation of these compositions are both well known in the art and commercially available and include synthetic culture media, inbred mice and the like. An exemplary synthetic medium is Dulbecco's minimal essential medium (DMEM; Dulbecco et al. (1959) *Virol.* 8:396) supplemented with 4.5 gm/1 glucose, 20 mM glutamine, and 20% fetal calf serum. An exemplary inbred mouse strain is the Balb/c.

Example 1 describes the production of murine anti-human CTLA4 monoclonal antibodies, which may be used in the subject methods and compositions. The ER5.4D3, ES5.3D6, ER5.3D8, ES5.4E3 and ER4.7G11 hybridomas, producing the ER5.4D3 (also referred to as 4D3 or CTLA4.1), ES5.3D6 (also referred to as 3D6 or CTLA4.2), ER5.3D8 (also referred to as 3D8 or CTLA4.3), ES5.4E3 (also referred to as 4E3 or CTLA4.4) and ER4.7G11 (also referred to as 7G11) antibodies, respectively, were deposited under the provisions of the Budapest Treaty with the American Type Culture Collection, Parklawn Drive, Rockville, Md., on Jun. 3, 1994. The ER5.4D3 hybridoma was assigned ATCC Accession Number HB 11645. The ES5.3D6 hybridoma was assigned ATCC Accession Number HB 11644. The ER5.3D8 hybridoma was assigned ATCC Accession Number HB 11641. The ES5.4E3 hybridoma was assigned ATCC Accession Number HB 11643. The ER4.7G11 hybridoma was assigned ATCC Accession Number HB 11642.

D. Chimeric and Humanized anti-CTLA4 Antibodies. When antibodies produced in non-human subjects are used therapeutically in humans, they are recognized to varying degrees as foreign and an immune response may be generated in the patient. One approach for minimizing or eliminating this problem, which is preferable to general immunosuppression, is to produce chimeric antibody derivatives, i.e., antibody molecules that combine a non-human animal variable region and a human constant region. Such antibodies are the equivalents of the monoclonal and polyclonal antibodies described above, but may be less immunogenic when administered to humans, and therefore more likely to be tolerated by the patient.

Chimeric mouse-human monoclonal antibodies (i.e., chimeric antibodies) reactive with CTLA4 can be produced by recombinant DNA techniques known in the art. For example, a gene encoding the constant region of a murine (or other species) anti-CTLA4 antibody molecule is substituted with a gene encoding a human constant region. (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., PCT Application WO 86/01533; Cabilly et al. U.S. Pat. No. 4,816,567; Cabilly et al., European Patent Application 125,023; Better et al. (1988 *Science* 240:1041-1043); Liu et al. (1987) *PNAS* 84:3439-3443; Liu et al. (1987) *J. Immunol.* 139:3521-3526; Sun et al. (1987) *PNAS* 84:214-218; Nishimura et al. (1987) *Canc. Res.* 47:999-1005; Wood et al. (1985) *Nature* 314:446-449; and Shawet al. (1988) *J. Natl Cancer Inst.* 80:1553-1559).

A chimeric antibody can be further "humanized" by replacing portions of the variable region not involved in antigen binding with equivalent portions from human variable regions. General reviews of "humanized" chimeric antibodies are provided by Morrison, S. L. (1985) *Science* 229:1202-1207 and by Oi et al. (1986) *BioTechniques* 4:214. Those methods include isolating, manipulating, and expressing the nucleic acid sequences that encode all or part of an immunoglobulin variable region from at least one of a heavy or light chain. Sources of such nucleic acid are well known to those skilled in the art and, for example, may be obtained from an anti-CTLA4 antibody producing hybridoma. The cDNA encoding the chimeric antibody, or fragment thereof, can then be cloned into an appropriate expression vector. Suitable "humanized" antibodies can be alternatively produced by CDR or CEA substitution (see U.S. Pat. No. 5,225,539 to Winter; Jones et al. (1986) *Nature* 321:552-525; Verhoeyan et al. (1988) *Science* 239:1534; and Beidler et al. (1988) *J. Immunol.* 141:4053-4060).

As an alternative to humanizing an mAb from a mouse or other species, a human mAb directed against a human protein can be generated. Transgenic mice carrying human antibody repertoires have been created which can be immunized with human CTLA4. Splenocytes from these immunized transgenic mice can then be used to create hybridomas that secrete human mAbs specifically reactive with human CTLA4 (see, e.g., Wood et al. PCT publication WO 91/00906, Kucherlapati et al. PCT publication WO 91/10741; Lonberg et al. PCT publication WO 92/03918; Kay et al. PCT publication 92/03917; Lonberg, N. et al. (1994) *Nature* 368:856-859; Green, L. L. et al. (1994) *Nature Genet.* 7:13-21; Morrison, S. L. et al. (1994) *Proc. Natl. Acad. Sci. USA* 81:6851-6855; Bruggeman et al. (1993) *Year Immunol* 7:33-40; Tuaillon et al. (1993) *PNAS* 90:3720-3724; Bruggeman et al. (1991) *Eur J Immunol* 21:1323-1326; and).

E. Combinatorial anti-CTLA4 Antibodies. Monoclonal antibody compositions of the invention can also be produced by other methods well known to those skilled in the art of recombinant DNA technology. An alternative method, referred to as the "combinatorial antibody display" method, has been developed to identify and isolate antibody fragments having a particular antigen specificity, and can be utilized to produce monoclonal anti-CTLA4 antibodies (for descriptions of combinatorial antibody display see e.g., Sastry et al. (1989) *PNAS* 86:5728; Huse et al. (1989) *Science* 246:1275; and Orlandi et al. (1989) *PNAS* 86:3833). After immunizing an animal with a CTLA4 immunogen as described above, the antibody repertoire of the resulting B-cell pool is cloned. Methods are generally known for directly obtaining the DNA sequence of the variable regions of a diverse population of immunoglobulin molecules by using a mixture of oligomer primers and PCR. For instance, mixed oligonucleotide primers corresponding to the 5' leader (signal peptide) sequences and/or framework 1 (FR1) sequences, as well as primer to a conserved 3' constant region primer can be used for PCR amplification of the heavy and light chain variable regions from a number of murine antibodies (Larrick et al. (1991) *Biotechniques* 11:152-156). A similar strategy can also been used to amplify human heavy and light chain variable regions from human antibodies (Larrick et al. (1991) *Methods: Companion to Methods in Enzymology* 2:106-110).

In an illustrative embodiment, RNA is isolated from activated B cells of, for example, peripheral blood cells, bone marrow, or spleen preparations, using standard protocols (e.g., U.S. Pat. No. 4,683,202; Orlandi, et al. *PNAS* (1989) 86:3833-3837; Sastry et al., *PNAS* (1989) 86:5728-5732; and Huse et al. (1989) *Science* 246:1275-1281.) First-strand cDNA is synthesized using primers specific for the constant region of the heavy chain(s) and each of the κ and λ light chains, as well as primers for the signal sequence. Using variable region PCR primers, the variable regions of both heavy and light chains are amplified, each alone or in combination, and ligated into appropriate vectors for further manipulation in generating the display packages. Oligonucleotide primers useful in amplification protocols may be unique or degenerate or incorporate inosine at degenerate positions. Restriction endonuclease recognition sequences may also be incorporated into the primers to allow for the cloning of the amplified fragment into a vector in a predetermined reading frame for expression.

The V-gene library cloned from the immunization-derived antibody repertoire can be expressed by a population of display packages, preferably derived from filamentous phage, to form an antibody display library. Ideally, the display package comprises a system that allows the sampling of very large variegated antibody display libraries, rapid sorting after each affinity separation round, and easy isolation of the antibody gene from purified display packages. In addition to commercially available kits for generating phage display libraries (e.g., the Pharmacia *Recombinant Phage Antibody System*, catalog no. 27-9400-01; and the Stratagene SurfZAP™ phage display kit, catalog no. 240612), examples of methods and reagents particularly amenable for use in generating a variegated anti-CTLA4 antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982.

In certain embodiments, the V region domains of heavy and light chains can be expressed on the same polypeptide, joined by a flexible linker to form a single-chain Fv fragment, and the scFV gene subsequently cloned into the desired expression vector or phage genome. As generally described in McCafferty et al., *Nature* (1990) 348:552-554, complete $V_H$ and $V_L$ domains of an antibody, joined by a flexible $(Gly_4$-$Ser)_3$ linker can be used to produce a single chain antibody which can render the display package separable based on antigen affinity. Isolated scFV antibodies immunoreactive with CTLA4 can subsequently be formulated into a pharmaceutical preparation for use in the subject method.

Once displayed on the surface of a display package (e.g., filamentous phage), the antibody library is screened with a CTLA4 protein, or peptide fragment thereof, to identify and isolate packages that express an antibody having specificity for CTLA4. Nucleic acid encoding the selected antibody can be recovered from the display package (e.g., from the phage genome) and subcloned into other expression vectors by standard recombinant DNA techniques.

F. Hybridomas and Methods of Preparation. Hybridomas useful in the present invention are those characterized as having the capacity to produce a monoclonal antibody which will specifically immunoreact with a CTLA4 antigen. As described below, the hybridoma cell producing anti-CTLA4 antibody can be directly implanted into the recipient animal in order to provide a constant source of antibody. The use of immuno-isolatory devices to encapsulate the hybridoma culture can prevent immunogenic response against the implanted cells, as well as prevent unchecked proliferation of the hybridoma cell in an immunocompromised host. A preferred hybridoma of the present invention is characterized as producing antibody molecules that specifically immunoreact with an epitope of a CTLA4 molecule expressed on the cell surfaces of activated human T cells which, upon ligation, induces apoptosis in the T cells.

Methods for generating hybridomas that produce, e.g., secrete, antibody molecules having a desired immunospecificity, i.e., having the ability to immunoreact with a particular CTLA4, and/or an identifiable epitope of CTLA4, are well known in the art. Particularly applicable is the hybridoma technology described by Niman et al. (1983) *PNAS* 80:4949-4953; and by Galfre et al. (1981) *Meth. Enzymol.* 73:3-46.

G. Additional Anti-CTLA4 Antibodies of the Invention: In addition to the CTLA4 antibodies of the invention which induce T cell apoptosis, the invention also provides anti-CTLA4 antibodies that cross react with CD28 (referred to herein as anti-CD28/CTLA4 antibodies, of which the 7G11 mAb is representative). Such antibodies can be produced by techniques described above and screened and identified as described in Example 1. In a preferred embodiment, the anti-CD28/CTLA4 antibody binds an epitope on CTLA4 includes or encompasses an amino acid sequence:

(Xaa)$_n$-Pro-Pro-Tyr-Tyr-Leu-(Xaa)$_n$ (SEQ ID NO: 34), wherein Xaa is any amino acid and n=0-20 (preferably 0-10, more preferably 0-5, even more preferably 0-3). In native human CTLA4, this sequence is located at amino acid positions 101to 105 of SEQ ID NO: 36. Xaa can be additional CTLA4 amino acid residues flanking this region or can be other residues, e.g., included to enhance solubility or immunogenicity of the peptide, as discussed above. A peptide containing a common CD28/CTLA4 epitope (e.g., SEQ ID NO: 34) can be used as an immunogen to raise an anti-CD28/CTLA4 antibody of the invention. Accordingly, the invention further encompasses an isolated CTLA4 peptide comprising an amino acid sequence: (Xaa)$_n$-Pro-Pro-Tyr-Tyr-Leu-(Xaa)$_n$ (SEQ ID NO: 34), wherein Xaa is any amino acid and n=0-20. The anti-CD28/CTLA4 antibody of the invention is useful for inducing a costimulatory signal in T cells as described in the Examples.

II. Other Agents that Induce T Cell Apoptosis

Alternative to an anti-CTLA4 antibody, or fragment thereof, apoptosis can be induced by an isolated form of a novel native CTLA4 ligand. As described in Example 5, T cell apoptosis can be induced by a novel, non-B7-1, non-B7-2, CTLA4-binding ligand present on the surface of a B lymphoblastoid cell line (LBL). A cDNA encoding this novel CTLA4 ligand can be isolated by expression cloning as described in Example 5. An apoptotic CTLA4 ligand so isolated can be expressed recombinantly by standard techniques, such as described above. In particular a soluble recombinant form of the native CTLA4 ligand can be expressed and isolated, for example by expression of the extracellular domain of the protein alone or as a fusion protein (e.g., an immunoglobulin fusion protein). An isolated soluble form of the native CTLA4 ligand capable of crosslinking an epitope on CTLA4 that induces T cell apoptosis can be used to clonally delete T cells according to the methods of the invention. Additionally, the novel CTLA4 ligand can be expressed on a cell surface and the cell expressing the CTLA4 ligand can be used to induce T cell apoptosis (e.g., the ligand can be expressed on allogeneic cells to clonally delete alloreactive T cells). Alternatively, an isolated form of the CTLA4 ligand that does not induce apoptosis (e.g., does not crosslink CTLA4) but binds to CTLA4 and inhibits its interaction with a native apoptotic CTLA4 ligand can be used to inhibit T cell apoptosis.

Modified forms of the known CTLA4 ligands B7-1 and B7-2 that bind only to CTLA4 but not CD28 and induce T cell apoptosis are also encompassed by the invention. Nucleic acid encoding B7-1 or B7-2 (e.g., cDNA) can be subjected to mutagenesis (e.g., random chemical mutagenesis, site-directed mutagenesis, polymerase chain reaction-mediated mutagenesis, etc.) and the mutated proteins encoded therein can be expressed recombinantly. A modified form of B7-1 or B7-2 can then be selected which no longer binds to CD28 (e.g., as assessed by ELISA) but which retains CTLA4 binding and which induces T cell apoptosis (e.g., assessed using a system such as that described in the Examples, e.g., the modified form of B7-1 or B7-2 expressed on CHO cells, in combination with anti-CD3 antibody treatment, induces apoptosis when cultured with activated T cells).

Peptide fragments of known or novel CTLA4 ligands, peptide mimetics and other small molecules (e.g., drugs) that bind to and crosslink an epitope on CTLA4 that induces T cell apoptosis are also within the scope of the invention. A small molecule inducer of T cell apoptosis can be identified by screening substances using a system such as that described in the Examples or by rational drug design, for example by designing a molecule to interact with an epitope on CTLA4 that induces T cell apoptosis (e.g., the epitope shown in SEQ ID NO: 33).

Another type of apoptotic agent contemplated by the invention is a nucleic acid encoding a CTLA4 apoptotic ligand as described herein. For example, nucleic acid (e.g., DNA) encoding an anti-CTLA4 antibody (or fragment thereof) that crosslinks an epitope on CTLA4 that induces apoptosis, or nucleic acid encoding a novel CTLA4 ligand (or portion thereof) that induces apoptosis, can be introduced into cells in vitro, or administered to a subject in vivo, as gene therapy to clonally delete activated T cells. Recombinant expression vectors for expressing proteins or peptides in cells (e.g., recombinant viral vectors), and nucleic acid delivery mechanisms suitable for gene therapy in vitro or in vivo, are well known in the art. An expression vector encoding a soluble, secreted form of anti-CTLA4 antibody, or other CTLA4 ligand, can be used to produce within cells a CTLA4 apoptotic ligand which is then secreted from the cells and binds to CTLA4 on activated T cells (e.g., in culture or in vivo) to induce apoptosis.

An alternative type of agent for inducing T cell apoptosis is one which acts intracellularly to trigger an apoptotic signal mediated by CTLA4. Thus, this agent does not bind to the extracellular portion of CTLA4, but rather mimics or induces an intracellular signal (e.g., second messenger) associated with ligation of CTLA4 by an apoptotic ligand. The apoptotic ligands described herein (e.g., anti-CTLA4 antibody) can be used to identify an intracellular signal(s) associated with apoptosis mediated by CTLA4 by contacting the CTLA4 with an activated T cell (as described in the Examples) and examining the resultant intracellular signalling that occurs (e.g., protein tyrosine phosphorylation, calcium influx, activation of serine/threonine and/or tyrosine kinases, phosphatidyl inositol metabolism, etc.). An agent which inhibits or enhances an intracellular signal associated with CTLA4-mediated apoptosis can then be used to modulate T cell apoptosis. Alternatively, agents (e.g., small molecules, drugs, etc.) can be screened for their ability to inhibit or enhance apoptosis using a system such as that described in the Examples.

III. Therapeutic Uses of CTLA4 Ligands that Induce T Cell Apoptosis

The CTLA4 ligands of the invention, e.g., crosslinking antibodies, or agents which act intracellularly to trigger an apoptotic signal mediated by CTLA4, can be used therapeutically to clonally delete activated T cells through induction of apoptosis in the T cells, thereby inhibiting T cell responses. Apoptotic ligands, or intracellular agents, can be identified by their ability to induce apoptosis when added to an in vitro culture of activated T cells in the presence of a TCR/CD3 stimulus, as described in the Examples. The TCR/CD3 stimulus can be antigen specific, such as antigen presented to a T cell clone by antigen presenting cells, or can be non-specific, such as crosslinking of CD3 by anti-CD3 antibodies. Apoptosis is typically assessed by measuring cellular DNA fragmentation, such as by detection of nucleosomal-length DNA fragments on agarose electrophoretic gels (see e.g., Quingsheng, T. et al. (1991) *Cell* 67:629-639). Other suitable assays of apoptosis include uptake of Hoechst 33342 dye (see e.g., Hardin, J. A. et al. (1992) J. Immunol. Methods 154:99-107), detection of nuclear DNA damage using the intercalating dye p-phenylenediamine (see e.g., Salcedo, T. W. et al. (1992) *J. Immunol. Methods* 148:209-216) and flow cytometry assays as described in Darzynkiewicz, Z. et al. (1992) *Cytometry* 13:795-808.

In addition to directly assessing the occurrence of apoptosis in a population of T cells, clonal deletion of T cells within a population of T cells, as a result of apoptosis, can be assessed by rechallenging the population of T cells with an antigenic stimulus and determining whether T cell responses, such as proliferation and/or cytokine production, occur. For example, apoptosis can be induced in alloreactive activated T cells within a T cell population by contact with allogeneic cells and a CTLA4 ligand of the invention. Subsequently, clonal deletion of the alloreactive T cells can be assessed by challenging the T cell population with the allogeneic cells and measuring T cell proliferation and/or cytokine (e.g., IL-2) production. T cell proliferation is typically measured by incorporation of tritiated thymidine, whereas cytokine production can be assessed by detection of the cytokine (e.g., IL-2) in the culture supernatant, such as by ELISA. Clonal deletion of alloreactive T cells is indicated by a lack of T cell responses to restimulation by allogeneic cells.

To induce apoptosis in an activated T cell according to the invention, an agent which stimulates a CTLA4-associated apoptotic signal is contacted with the T cell. This agent can act by crosslinking an epitope on CTLA4 that induces apoptosis (e.g., an epitope comprising the amino acid sequence shown in SEQ ID NO: 33) or can act intracellularly to induce an apoptotic signal associated with a CTLA4-mediated apoptotic pathway. A preferred crosslinking agent is an anti-CTLA4 antibody of the invention, such as an anti-human CTLA4 monoclonal antibody. However, other agents (e.g., soluble native CTLA4 ligands, chemical agents etc.) that can crosslink CTLA4 to produce the desired results (i.e., apoptosis) can also be used. An activated T cell (i.e., a T cell that has previously been stimulated to express CTLA4 on its surface, either in an antigen specific manner or in a non-specific manner) can be induced to undergo apoptosis by contact with a CTLA4 ligand of the invention or other agent that crosslinks an epitope on CTLA4 that induces apoptosis or generates an intracellular signal associated with apoptosis. To undergo apoptosis, in addition to induction of a CTLA4-associated signal (e.g., by crosslinking CTLA4), the T cell also requires stimulation through another surface molecule(s), in particular the TCR/CD3 complex, e.g., by contact with antigen or with a non-specific stimulus such as an anti-CD3 antibody. When antigen is used to stimulate the T cell through its T cell receptor (TCR), antigen specific apoptosis results. Thus, the invention provides methods for inducing antigen specific apoptosis in activated T cells. The ability of apoptotic CTLA4 ligands to clonally delete T cells in an antigen specific manner can be used to inhibit specific antigenic T cell responses and to produce long term antigen specific immunosuppression and/or tolerance. Stimulation of other T cell surface molecules in conjunction with stimulation of a CTLA4-associated apoptotic signal may also induce T cell apoptosis in an antigen nonspecific manner.

T cells can be clonally deleted by induction of apoptosis according to the methods of the invention either in vitro or in vivo. To induce T cell apoptosis in vitro, activated T cells are contacted both with a first agent that stimulates the T cell through a TCR/CD3 complex and a second agent which stimulates a CTLA4-associated apoptotic signal, such as an agent that crosslinks an epitope on CTLA4 that induces apoptosis in the T cell (e.g., a CTLA4 ligand of the invention or other CTLA4 crosslinking agent). The first agent can be a non-specific agent, such as an anti-CD3 antibody, to induce polyclonal T cell apoptosis. More preferably, antigen specific apoptosis is induced by stimulating the T cell through the TCR with antigen, for example antigen presented by an antigen presenting cell or alloantigen on the surface of allogeneic cells (i.e., the first agent is antigen presented to the T cell in a form suitable to stimulate a signal through the TCR). In a preferred embodiment, the second agent is an anti-CTLA4 antibody, preferably a monoclonal antibody.

To induce T cell apoptosis in vivo, an agent which stimulates a CTLA4-associated apoptotic signal in the T cell (e.g., an agent that crosslinks an epitope on CTLA4 that induces apoptosis in the T cell) is administered to a subject. In this case, activated T cells receive the required stimulation through the TCR/CD3 complex by an endogeneous stimulus in vivo (e.g., an autoantigen or foreign antigen presented by antigen presenting cells in vivo). Alternatively, an antigenic stimulus can be coadministered with the CTLA4 crosslinking agent (e.g., to induce apoptosis in allergen-specific T cells, the allergen can be coadministered with the CTLA4 crosslinking agent or to induce apoptosis in autoantigen-specific T cells, the autoantigen can be coadministered). A preferred CTLA4 crosslinking agent for administration to a subject to induce T cell apoptosis is an anti-CTLA4 antibody of the invention, preferably an anti-CTLA4 monoclonal antibody.

When T cell apoptosis is induced in vivo by administration of an agent that stimulates a CTLA4-associated apoptotic signal to a subject, additional treatment of the subject may be necessary to inhibit or block stimulatory signals delivered to T cells in the microenvironment in vivo which promote T cell proliferation and/or other T cell responses. For example, as described in Example 4, the presence of the lymphokine interleukin-2 (IL-2) can inhibit induction of apoptosis mediated by crosslinking of CTLA4. Accordingly, in the methods for inducing T cell apoptosis, it may be beneficial to also inhibit the production or function of T cell growth factors (e.g., IL-2) in the subject. Thus, in addition to an agent that stimulates a CTLA4-associated apoptotic signal, another agent which inhibits production or function of T cell growth factors may be administered to the subject to promote T cell apoptosis. Examples of suitable agents for inhibiting the production or function of T cell growth factors include an anti-IL-2 antibody, an anti-IL-2 receptor antibody or an immunosuppressive drug which reduces IL-2 levels in the subject, such as cyclosporin A.

Additionally or alternatively, in order to induce apoptosis in a subject, it may also be beneficial to inhibit or prevent T cells from receiving a costimulatory signal in vivo, such as the costimulatory signal mediated by the interaction of CD28 with either B7-1 or B7-2. Accordingly, in addition to administering an agent that stimulates a CTLA4-associated apoptotic signal to a subject, another agent which inhibits generation of a costimulatory signal in T cells, such as a blocking molecule which binds to CD28, B7-1 or B7-2, may also be administered to the subject. Examples of suitable blocking molecules include an anti-CD28 Fab fragment, anti-B7-1 or anti-B7-2 blocking antibodies (i.e., antibodies which block CD28-B7-1/B7-2 interactions but do not induce a costimulatory signal in T cells) and soluble forms of CD28, B7-1 or B7-2 (e.g., immunoglobulin fusion proteins that block CD28-B7-1/B7-2 interactions but do not induce a costimulatory signal in T cells). Additionally, combinations of blocking molecules, e.g. an anti-B7-1 antibody and an anti-B7-2 antibody may be used.

The methods of the invention for inducing T cell apoptosis are applicable to a variety of clinical situations where it is desirable to clonally delete a specific population of reactive T cells, as described in greater detail in the subsections below.

A. Organ Transplantation/GVHD: Clonal deletion of alloreactive T cells by induction of alloantigen specific apoptosis in activated T cells is useful in situations of cellular, tissue, skin and organ transplantation and in bone marrow transplantation (e.g., to inhibit graft-versus-host disease (GVHD)). For example, deletion of alloreactive T cells may result in reduced tissue destruction in tissue transplantation and long-term graft acceptance without the need for generalized immunosuppression. Typically, in tissue transplants, rejection of the graft is initiated through its recognition as foreign by T cells, followed by an immune reaction that destroys the graft. Administration to a transplant recipient of an agent that stimulates a CTLA4-associated apoptotic signal, such as a monoclonal anti-CTLA4 antibody of the invention, together with the transplanted cells may induce apoptosis in alloreactive T cells of the recipient which become activated by the transplanted foreign cells. The treatment regimen can involve "presensitizing" (i.e., activating) alloreactive T cells of the recipient to donor antigens by administration of a sample of donor cells (e.g., hematopoietic cells) to the recipient prior to transplantation. This pretreatment activates donor specific alloreactive T cells in the recipient to become CTLA4$^+$ and thus capable of being clonally deleted upon reexposure to donor antigens (e.g., on the graft) in the presence of an agent that stimulates a CTLA4-associated apoptotic signal.

An alternative treatment regimen can involve exposing T cells of the recipient in vitro to donor cells (e.g., hematopoietic cells of the graft donor) prior to transplantation of the graft into the recipient in order to activate alloantigen specific T cells (i.e., induce CTLA4 on the surface of the alloreactive cells) and, once activated, contacting the recipient T cells in vitro both with donor cells and an agent that stimulates a CTLA4-associated apoptotic signal (e.g., anti-CTLA4 mAb), thereby inducing apoptosis in the activated alloreactive cells. Once alloreactive T cells have been clonally deleted in vitro, the remaining T cells can be readministered to the recipient and transplantation performed. Additional CTLA4 crosslinking agent can be administered to the subject to induce apoptosis in any alloreactive T cells that may remain in vivo (i.e., a combination in vitro depletion, in vivo treatment approach can be utilized).

The approaches described above can similarly be applied to the situation of bone marrow transplantation to specifically deplete alloreactive T cells from donor bone marrow. Removal of alloreactive T cells from the graft while preserving the presence of other T cells is beneficial for inhibiting the occurrence of graft versus host disease, promoting bone marrow engraftment in the transplant recipient and preserving the anti-leukemia activity (i.e., the graft versus leukemia response) of donor cells in the graft. To clonally delete alloreactive T cells in the graft, donor bone marrow can be incubated prior to transplantation in vitro with cells from the recipient (e.g., hematopoietic cells) to activate alloreactive T cells in the bone marrow. Following activation, alloreactive T cells can be clonally deleted from the bone marrow by incubation in vitro both with recipient cells and an agent that stimulates a CTLA4-associated apoptotic signal. Additional agents that inhibit the generation of stimulatory signals in the T cells (e.g., anti-B7-1 and/or anti-B7-2 antibodies, an anti-IL-2Rantibody etc, as described above) can be included in the incubation. Bone marrow specifically depleted of alloreactive cells is then administered to the recipient, who may further be treated with the agent that stimulates a CTLA4-associated apoptotic signal in vivo to induce apoptosis in any remaining alloreactive cells in vivo. Additional treatments which inhibit the generation of a costimulatory signal in T cells in the recipient, or inhibit the production or function of a T cell growth factor(s) (e.g., IL-2) in the recipient can also be administered in vivo to further promote the induction of T cell apoptosis in the recipient.

The efficacy of a particular agent that stimulates a CTLA4-associated apoptotic signal (e.g., anti-CTLA4 antibody) in preventing organ transplant rejection or GVHD can be assessed using animal models that are predictive of efficacy in humans. Given the homology between CTLA4 molecules of different species, the functionally important aspects of CTLA4 are believed to be conserved structurally among species thus allowing animal systems to be used as models for efficacy in humans. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al., Science, 257: 789-792 (1992) and Turka et al., Proc. Natl. Acad. Sci. USA, 89: 11102-11105 (1992). In addition, murine models of GVHD (see Paul ed., Fundamental Immunology, Raven Press, New York, 1989, pp. 846-847) can be used to determine the effect of inducing T cell apoptosis via a CTLA4-associated apoptotic signal (by in vitro and/or in vivo treatment of T cells) on the development of that disease.

As an illustrative embodiment, an anti-CTLA4 antibody can be used in a rat model of organ transplantation to ascertain the ability of the antibody to block alloantigen responses in vivo. Recipient Lewis rats receive a Brown-Norway rat strain cardiac allograft which is anastamosed to vessels in the neck as described in Bolling, S. F. et al., *Transplant*, 453:283-286 (1992). Grafts are monitored for mechanical function by palpation and for electrophysiologic function by electrocardiogram. Graft rejection is said to occur on the last day of palpable contractile function. As an initial test, animals are treated with daily injections of anti-CTLA4 monoclonal antibody or an isotype-matched control monoclonal antibody for 7 days. Antibodies are administered at a dosage range between approximately 0.015 mg/day and 0.5 mg/day. In parallel experiments, prior to cardiac allografting, recipient Lewis rats receive a sample of Brown-Norway cells (e.g., peripheral blood cells or spleen cells) to activate alloreactive T cells in the recipients. Following this presensitization step, the allograft is transplanted together with administration of an anti-CTLA4 antibody. Untreated Lewis rats typically reject heterotopic Brown-Norway allografts in about 7 days. The rejection of allografts by antibody-treated animals is assessed in comparison to untreated controls.

An untreated animal and an antibody treated animal are sacrificed for histological examination. Cardiac allografts are removed from the untreated animal and the antibody treated animal four days after transplantation. Allografts are fixed in formalin, and tissue sections are stained with hematoxylin-eosin. The heart tissue of the untreated and treated animals is examined histologically for severe acute cellular rejection including a prominent interstitial mononuclear cell infiltrate with edema formation, myocyte destruction, and infiltration of arteriolar walls. The effectiveness of the antibody treatment in inhibiting graft rejection is supported by a lack of an acute cellular rejection in the heart tissue of antibody treated animals.

To determine whether antibody therapy establishes long term graft acceptance that persists following antibody treatment, animals treated for 7 days with daily injections of antibody are observed without additional therapy until cessation of graft function. Animals receive either no treatment, anti-CTLA4 antibody or an isotype-matched control monoclonal antibody. Antibody treatment is initiated at the time of transplantation and continues for 7 days. Graft survival is assessed daily as described above. Allografts are examined histologically from animals in which the graft stops functioning as described above. Induction of graft tolerance by antibody treatment is indicated by the continued functioning of the graft following the cessation of antibody treatment.

After prolonged graft acceptance, an antibody-treated animal can be sacrificed and the lymphocytes from the recipient can be tested for their functional responses. These responses are compared with those of lymphocytes from a control (non-transplanted) Lewis rat, and results are normalized as a percentage of the control response. The T cell proliferative response to ConA and to cells from a Brown-Norway rat and a third party ACI rat can be examined. Additionally, the thymus and spleen from the untreated and treated animals can be compared in size, cell number and cell type (e.g. by flow cytometic analyses of thymus, lymph nodes and spleen cells). Specific nonresponsiveness in the treated animals to alloantigens, as a result of specific clonal deletion of alloreactive cells, is indicated by the ability of the T cells to respond to ConA and third party stimulators (e.g., ACI rat cells) but not to Brown-Norway rat cells.

B. Autoimmune Diseases: Clonal deletion of T cells by induction of antigen specific T cell apoptosis may also be therapeutically useful for treating autoimmune diseases. Many autoimmune disorders are the result of inappropriate activation of T cells that are reactive against self tissue (i.e., reactive against autoantigens) and which promote the production of cytokines and autoantibodies involved in the pathology of the diseases. Preventing the activation of autoreactive T cells thus may reduce or eliminate disease symptoms. Administration of an agent that stimulates a CTLA4-associated apoptotic signal, such as an anti-CTLA4 antibody of the invention, which binds to an epitope on CTLA4 that induces T cell apoptois can be used to delete autoreactive T cells, thereby inhibiting T cell responses and preventing production of autoantibodies or T cell-derived cytokines which may be involved in the disease process. Additionally, since autoreactive T cells can be eliminated rather than simply tolerized, long-term relief from the disease may be achievable.

To treat an autoimmune disorder, an agent that stimulates a CTLA4-associated apoptotic signal (e.g., CTLA4 ligand of the invention) is administered to a subject in need of treatment. Autoreactive T cells, previously activated by autoantigen in vivo, will be induced to undergo apoptosis upon antigenic stimulation by autoantigen in vivo. Alternatively, for autoimmune disorders with a known autoantigen, the autoantigen can be coadministered to the subject with the apoptotic agent. Since only activated T cells are eliminated by this treatment, resting T cells specific for other antigens should be unaffected by the treatment.

This method can be used to treat a variety of autoimmune diseases and disorders having an autoimmune component, including diabetes mellitus, arthritis (including rheumatoid arthritis, juvenile rheumatoid arthritis, osteoarthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjögren's Syndrome, including keratoconjunctivitis sicca secondary to Sjögren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves ophthalmopathy, sarcoidosis, primary biliary cirrhosis, uveitis posterior, and interstitial lung fibrosis.

The efficacy of CTLA4 crosslinking agents in preventing or alleviating autoimmune disorders can be determined using a number of well-characterized animal models of human autoimmune diseases. Examples include murine experimental autoimmune encephalitis, systemic lupus erythmatosis in MRL/lpr/lpr mice or NZB hybrid mice, murine autoimmune collagen arthritis, diabetes mellitus in NOD mice and BB rats, and murine experimental myasthenia gravis (see Paul ed., *Fundamental Immunology*, Raven Press, New York, 1989, pp. 840-856).

Experimental Autoimmune Encephalomyelitis (EAE) is a rodent and primate model for multiple sclerosis. In an illustrative embodiment, in the passive EAE model, donor mice are immunized with 0.4 mg Myelin Basic Protein (MBP) in Complete Freund's Adjuvant (CFA), divided over four quadrants. The draining axillary and inguinal lymph nodes are removed eleven days later. Lymph node cells ($4 \times 10^6$/ml) are plated in 2 ml cultures in 24 well plates, in the presence of 25 µg/ml MBP. After four days in culture, $30 \times 10^6$ of the treated cells are injected into the tail vein of each naive, syngeneic recipient mouse.

The recipient mice develop a remitting, relapsing disease and are evaluated utilizing the following criteria:

0 normal, healthy 1 limp tail, incontinence; occasionally the first sign of the disease is a "tilt"

2 hind limb weakness, clumsiness 3 mild paraparesis 4 severe paraparesis 5 quadriplegia 6 death Using the passive model of EAE, the effect of anti-CTLA4 antibody treatment of the donor cells on resulting disease severity in a recipient animal is tested in mice (e.g., the PLSJLF1/J strain). Culture of lymph node cells in vitro with MBP is performed either in the presence or the absence of about 30 μg/ml of an anti-CTLA4 antibody. The treated cells are then introduced into a syngeneic recipient mouse. The effect of antibody treatment of donor cells on the severity of the recipient's first episode of disease as compared to mice receiving untreated cells can be determined using the above-described criteria to assess disease severity. In addition, ensuing relapses in the mice receiving antibody-treated cells versus untreated cells can be assessed using the above-described criteria.

The effect of treating both the donor mice and the cultured donor cells with an anti-CTLA4 antibody on the clinical disease severity in the recipient can further be assessed. In these experiments, donor mice (e.g., of the SJL/J strain) immunized with MBP are given either 100 μg of an anti-CTLA4 antibody (alone or in combination) or 100 μg of an isotype matched control antibody intraperitoneally each day for eleven days. Cells are then isolated from lymph nodes of these donors and cultured with MBP in vitro in the presence of either 30 μg/ml of an anti-CTLA4 antibody (alone or in combination) or a control antibody. The treated cells are then introduced into a syngeneic recipient. The effect of antibody treatment on the severity of the ensuing disease in the recipient is then assessed using the above-described criteria.

Studies using a direct (active) model of EAE can also conducted. In these experiments, an anti-CTLA4 antibody is directly administered to mice immunized with MBP and treated with pertussis toxin (PT). Mice (e.g., the PLSJLFI/J strain) are immunized with MBP on day 0, injected with PT intravenously on days 0 and 2, and given either an anti-CTLA4 antibody or an isotype matched control antibody on days 0 to 7. The effect of direct antibody treatment of the MBP-immunized mice on the severity of the ensuing disease is then assessed using the above-described criteria.

C. Allergy: The IgE antibody response in atopic allergy is highly T cell dependent and, thus, clonal deletion of allergen specific T cells by induction of apoptosis may be useful therapeutically in the treatment of allergy and allergic reactions. For example, an anti-CTLA4 antibody can be administered to an allergic subject exposed to an allergen to induce apoptosis in allergen specific T cells, thereby downmodulating allergic responses in the subject. Administration of an agent that stimulates a CTLA4-associated apoptotic signal to an allergic subject may be accompanied by environmental exposure to the allergen or by coadministration of the allergen to the subject. Allergic reactions may be systemic or local in nature, depending on the route of entry of the allergen and the pattern of deposition of IgE on mast cells or basophils. Thus, it may be necessary to induce allergen specific T cell apoptosis locally or systemically by proper administration of an agent that stimulates a CTLA4-associated apoptotic signal (e.g., anti-CTLA4 antibody). For example, in one embodiment, an anti-CTLA4 antibody and an allergen are coadministered subcutaneously to an allergic subject.

D. Virally Infected or Malignant T Cells: The methods of inducing T cell apoptosis by crosslinking of CTLA4 can be applied to any T cell expressing CTLA4 on its surface. In addition to T cells activated by exposure to a specific antigen, other forms of T cells express CTLA4 on their surface. For example, virally infected T cells, such as those infected by HTLV-I or HIV, can be CTLA4$^+$ (see Freeman, G. J. et al. (1992) *J. Immunol.* 149:3795-3801; Haffar, O. K. et al. (1993) *Proc. Natl. Acad. Sci. USA* 90:11094-11098). Accordingly, CTLA4$^+$ virally infected T cells can be eliminated by inducing CTLA4-mediated apoptosis in the T cells. For example, CTLA4$^+$ virally infected T cells obtained from a subject can be cultured in vitro with an anti-CTLA4 antibody of the invention together with anti-CD3 antibodies to induce apoptosis. Following depletion of virally infected cells, the remaining T cell population can be expanded in vitro by conventional techniques and readministered to the subject. Additionally, malignant T cells expressing CTLA4 on their surface can be eliminated by induction of apoptosis in the T cells as described herein.

E. Antigen-Specific Clonal Deletion: The methods of the invention for inducing T cell apoptosis can essentially be applied to any antigen (e.g., protein) to clonally delete T cells responsive to that antigen in a subject. Thus, a subject can be primed with the antigen to activate antigen-specific T cells (i.e., induce CTLA4 on the surface of antigen specific T cells) and then when rechallenged with the antigen, an agent that stimulates a CTLA4-associated apoptotic signal is coadministered with the antigen to induce antigen specific T cell apoptosis. The antigen may be administered in a soluble form or attached to a carrier or support (e.g., a bead). This basic approach has widespread application as an adjunct to therapies which utilize a potentially immunogenic molecule for therapeutic purposes. For example, an increasing number of therapeutic approaches utilize a proteinaceous molecule, such as an antibody, fusion protein or the like, for treatment of a clinical disorder. A limitation to the use of such molecules therapeutically is that they can elicit an immune response directed against the therapeutic molecule in the subject being treated (e.g., the efficacy of murine monoclonal antibodies in human subjects is hindered by the induction of an immune response against the antibodies in the human subject). The method of the invention for inducing antigen specific T cell apoptosis can be applied to these therapeutic situations to enable long term usage of the therapeutic molecule in the subject without elicitation of an immune response. For example, a therapeutic antibody (e.g., murine mAb) is administered to a subject (e.g., human), which typically activates T cells specific for the antibody in the subject. To clonally delete these activated T cells, the therapeutic antibody is readministered to the subject together with an agent that stimulates a CTLA4-associated apoptotic signal, thereby inducing antigen specific apoptosis in the T cells. Clonal elimination of these activated T cells should then allow for continued efficacy of the therapeutic antibody in the subject.

IV. Therapeutic Uses of CTLA4 Ligands that Inhibit T Cell Apoptosis

In addition to providing a means to induce apoptosis in T cells, the invention also provides means for inhibiting T cell apoptosis by interfering with the generation of a CTLA4-associated apoptotic signal in the T cell. This signal can be inhibited, for example, by interfering with an interaction between CTLA4 on a T cell and a CTLA4 ligand on an antigen presenting cell that induces T cell apoptosis. Alternatively, an agent that acts intracellularly to block or inhibit the apoptotic signal can be used to inhibit apoptosis. Thus, apoptosis in a T cell is inhibited by contacting the T cell (e.g., by incubation in vitro or administration in vivo) with an agent that inhibits a CTLA4-associated apoptotic signal in the T cell, such as by inhibiting an interaction between CTLA4 on the T cell and a CTLA4 ligand that induces apoptosis. Preferably, the agent blocks the interaction of the CTLA4 ligand with an epitope on CTLA4 that induces T cell apoptosis, such as an epitope comprising an amino acid sequence shown in SEQ ID NO: 33. The agent can be, for example, a soluble CTLA4 protein (or portion thereof), a soluble CTLA4 fusion protein or an anti-CTLA4 antibody, or fragment thereof, which binds to CTLA4 but does not induce apoptosis. Preferred agents for inhibiting apoptosis include Fab fragments of anti-CTLA4 antibodies of the invention (or other non-crosslinking antibody fragments) and CTLA4Ig fusion proteins (e.g., CTLA4Ig), both of which can inhibit T cell apoptosis as described in Example 5. Alternatively, the agent can be a soluble form of the CTLA4 ligand, a soluble fusion protein of the CTLA4 ligand or an anti-CTLA4 ligand antibody, or fragment thereof. Additionally, peptide fragments or peptide mimetics can be use to inhibit interaction of CTLA4 with an apoptotic ligand. For example, a peptide encompassing an apoptotic epitope on CTLA4 (e.g., encompassing the amino acid sequence of SEQ ID NO: 33) can be used to inhibit an interaction between cell-surface CTLA4 and a natural ligand that binds to this epitope on CTLA4. Accordingly, the peptides of the invention encompassing a CTLA4 apoptotic epitope are also useful for inhibiting apoptosis in a T cell.

Inhibition of T cell apoptosis may be therapeutically useful for enhancing, prolonging and/or maintaining immune responses which naturally would be downmodulated by CTLA4-mediated apoptosis. For example, anti-tumor responses may naturally be downmodulated by clonal elimination of tumor specific T cells through CTLA4 mediated apoptosis (e.g., T cell apoptosis may be induced by expression of an apoptotic CTLA4 ligand on the surface of tumor cells). Accordingly, anti-tumor responses may be enhanced by inhibiting an interaction between CTLA4 and an apoptotic CTLA4 ligand by, for example, administering a blocking agent, as described above, to a tumor-bearing subject. Additionally, T cell responses to pathogens, such as viruses, bacteria, fungi, parasites and the like, may be enhanced and prolonged by inhibiting CTLA4 mediated T cell apoptosis as described herein. The efficacy of vaccination may also be increased by blocking CTLA4 mediated apoptosis according to the invention. For example, the vaccine can be administered together with an agent that blocks T cell apoptosis (e.g., an anti-CTLA4 mAb Fab fragment) to enhance to immune response against the vaccinating material.

In another application, inhibition of T cell apoptosis can be used to preserve T cells in a subject, such as a subject infected with a virus associated with T cell destruction, such as HIV. In HIV infections, CTLA4 expression on the surface of virally infected T cells, such as HIV infected T cells, may lead to destruction of the cells in vivo via CTLA4 mediated apoptosis. This destruction of the virally infected T cells, with the concomitant release of virus in vivo, may promote further infection of bystander T cells with the virus, thereby inhibiting the ability of the T cells to mount an immune response against the virus. Additionally, non-infected T cells in the subject may be deleted by a CTLA4-dependent apoptotic mechanism, further depleting the T cell population. Thus, administration to the subject of an agent which inhibits CTLA4 mediated apoptosis may be beneficial in controlling the spread of virus and in preserving the T cell population in HIV-infected subjects.

V. Administration of Therapeutic Forms of CTLA4 Ligands

The CTLA4 ligands of the invention (e.g., anti-CTLA4 antibodies) are administered to subjects in a biologically compatible form suitable for pharmaceutical administration in vivo to induce T cell apoptosis. By "biologically compatible form suitable for administration in vivo" is meant a form of the protein to be administered in which any toxic effects are outweighed by the therapeutic effects of the ligand. The term subject is intended to include living organisms in which an immune response can be elicited, e.g., mammals. Examples of subjects include humans, monkeys, dogs, cats, mice, rats, and transgenic species thereof. Administration of a ligand of the invention as described herein can be in any pharmacological form including a therapeutically active amount of CTLA4 ligand alone or in combination with another therapeutic molecule (e.g., anti-IL2 receptor antibody or CD28, B7-1 or B7-2 blocking antibody etc., as described above) and a pharmaceutically acceptable carrier. Administration of a therapeutically active amount of the therapeutic compositions of the present invention is defined as an amount effective, at dosages and for periods of time necessary to achieve the desired result. For example, a therapeutically active amount of an anti-CTLA4 antibody may vary according to factors such as the disease state, age, sex, and weight of the individual, and the ability of antibody to elicit a desired response in the individual. Dosage regimens may be adjusted to provide the optimum therapeutic response. For example, several divided doses may be administered daily or the dose may be proportionally reduced as indicated by the exigencies of the therapeutic situation.

The active compound (e.g., antibody) may be administered in a convenient manner such as by injection (subcutaneous, intravenous, etc.), oral administration, inhalation, transdermal application, or rectal administration. Depending on the route of administration, the active compound may be coated in a material to protect the compound from the action of enzymes, acids and other natural conditions which may inactivate the compound.

To administer a CTLA4 ligand by other than parenteral administration, it may be necessary to coat the ligand with, or co-administer the ligand with, a material to prevent its inactivation. A CTLA4 ligand may be administered to an individual in an appropriate carrier or diluent, co-administered with enzyme inhibitors or in an appropriate carrier such as liposomes. Pharmaceutically acceptable diluents include saline and aqueous buffer solutions. Enzyme inhibitors include pancreatic trypsin inhibitor, diisopropylfluorophosphate (DEP) and trasylol. Liposomes include water-in-oil-in-water emulsions as well as conventional liposomes (Strejan et al., (1984) *J. Neuroimmunol* 7:27).

The active compound may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, asorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., anti-CTLA4 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (e.g., antibody) plus any additional desired ingredient from a previously sterile-filtered solution thereof.

When the active compound is suitably protected, as described above, the compound may be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

VI. Identification of Additional Molecules Involved in CTLA4-Mediated T Cell Apoptosis The invention discloses a functional role for CTLA4 in the induction of apoptosis in a T cell. Apoptosis in a T cell may be mediated directly by CTLA4 upon ligation by a CTLA4 ligand, or alternatively, a CTLA4 associated molecule may be responsible for delivering an apoptotic signal to the T cell. CTLA4 associated molecules can be identified by a number of techniques known in the art. For example, the CTLA4 antibodies of the invention can be used in immunoprecipitation assays to identify molecules which coimmunoprecipitate with CTLA4. Proteins expressed by activated T cells can be radiolabelled (e.g., with $^{35}$S-methionine, or with $^{125}$I to label surface proteins) and then a CTLA4 antibody described herein can be used to immunoprecipitate proteins from the T cells. Immunoprecipitation techniques are well known in the art and are described, for example, in Ausubel, F. et al. (eds.), *Current Protocols in Molecular Biology*, John Wiley & Sons: New York, 1989, Section 10.16. Molecules that associate either intracellularly or at the cell surface with CTLA4 can be identified by coimmunoprecipitation with CTLA4 (e.g., detected by eletrophoretic analysis of immunoprecipitated proteins). Such a CTLA4-associated molecule can then be further purified and characterized based upon its interaction with CTLA4.

Alternatively, an expression cloning approach can be used to identify molecules which associate with CTLA4. It has previously been found that recombinant CTLA4, as a transmembrane form, cannot be stably expressed in host cells such as COS or CHO cells by standard techniques (although it can be expressed as a gpi-linked form as described in Example 1), suggesting that an additional molecule(s) is needed to achieve stable surface expression of CTLA4. Accordingly, this characteristic can be exploited to identify molecules which enable surface expression of transmembrane CTLA4 in a host cell. For example, a cDNA expression library can be prepared from an activated T cell as described in Example 5. This expression library is then cotransfected into host cells (e.g., COS cells) together with an expression vector encoding the transmembrane form of CTLA4. Transfected cells which express CTLA4 on their surface can then be selected, for example by panning or immunomagnetic bead separation using an anti-CTLA4 antibody of the invention (methods described in Example 5 can be used for cell transfection and isolation of CTLA4-expressing clones). cDNA encoding a CTLA4 associated molecule can be isolated from the selected cells.

This invention is further illustrated by the following examples which should not be construed as limiting. The contents of all references, patents and published patent applications cited throughout this application are hereby incorporated by reference.

EXAMPLE 1

Production and Screening of Anti-CTLA4 Monoclonal Antibodies

Production of Monoclonal Antibodies to human CTLA4

Balb/c female mice (obtained from Taconic, Germantown, N.Y.) were immunized subcutaneously and intraperitoneally with either 50 µg per mouse of recombinant human *E. coli*-expressed CTLA4 (extracellular domain only) emulsified in complete Freund's adjuvant (Sigma Chemical Company, St. Louis, Mo.) for ER series mice or $2 \times 10^6$ PMA/ionomycin-activated human T cells (obtained from Leukopaks) per mouse for ES series mice. The mice were boosted with 20-25 µg/mouse human recombinant CTLA4 emulsified in incomplete Freund's adjuvant (Sigma Chemical Company, St. Louis, Mo.) or $10^6$ PMA/ionomycin-activated human T cells at 14 day intervals following the initial immunizations. The mice were bled from the tail vein and the sera assayed for the presence of antibodies reactive to the immunogen by ELISA against the immunizing protein. Mice showing a strong serological titre were boosted intravenously with 50 µg recombinant human CTLA4 per mouse diluted in phosphate-buffered saline, pH 7.2 (GIBCO, Grand Island, N.Y.). Three to four days following the boost, the spleens from these mice were fused at a 5:1 ratio with SP 2/0-Ag 14 myeloma cells (ATCC, Rockville. Md.) with PEG 1450 (ATCC, Rockville. Md.) and plated onto 96 well plates containing irradiated MRC-5 fibroblast cells (ATCC, Rockville. Md.) in Dulbecco's modified Eagle's media (GIBCO, Grand Island, N.Y.) containing 25% CPSR-3 (Sigma Chemical Company), 2 mM L-glutamine, 50 U/ml penicillin, 50 µg/ml streptomycin, 20 µg/ml gentamycin, 0.25 µg/ml fungizone, and 10% NCTC-109 (GIBCO, Grand Island, N.Y.). Selection of hybridomas was done in the presence of hypoxanthineaminopterin-thymidine (ATCC, Rockville. Md.). As hybridoma colonies grew out in the next 10-21 days, supernatant from the wells was screened on 96 well flat-bottomed EIA plates (Costar, Cambridge, Mass.) coated with recombinant human CTLA4 as a primary screen. Secondary screening was done by flow cytometry on human CTLA4-transfected CHO cells and PMA/ionomycin activated human T cells. Hybridoma supernatants identified as containing antibodies directed towards CTLA4 were expanded and subcloned twice prior to ascites production and antibody purification by Protein A-Sepharose affinity chromatography.

Primary Screening of mAbs: ELISA Protocol

Each well of a 96 well flat bottomed EIA plate (Costar, Cambridge, Mass.) was coated with 50 µl per well of a 1 µg/ml recombinant human CTLA4 solution made in phosphate-buffered saline, pH 7.2, overnight at 4° C. The CTLA4 solution was aspirated off and the wells were blocked with 100 µl of 1% BSA in phosphate-buffered saline, pH 7.2 for 1 hour at room temperature. Following this blocking incubation, the wells were washed 3× with phosphate-buffered saline, pH 7.2 and 50 µl hybridoma supernatant was added per well and incubated 45 minutes at 37° C. Following this incubation, the wells were washed 3× with phosphate-buffered saline, pH 7.2 and then incubated with 50 µl per well of a 1:4000 dilution of horseradish peroxidase-conjugated affinity purified Goat anti-Mouse IgG (H&L) specific antibodies (Zymed Laboratories, San Francisco, Calif.) for 45 minutes at 37° C. The wells were then washed 3× with phosphate-buffered saline, pH 7.2 followed by a 30 minute incubation in 50 µl per well of 1 mM ABTS (2,2 azino-bis-3-ethylbenzthiazole-6-sulfonic acid) in 0.1 M sodium citrate, pH 4.2, to which a 1:1000 dilution of 30% hydrogen peroxide has been added as a substrate for the HRP to detect bound antibody. The absorbance was then determined at 410 nm on a spectrophotometer (Molecular Devices Corp, Menlo Park, Calif.).

Secondary Screening of mAbs: Flow Cytometry

Secondary screening was done by flow cytometry on human CTLA4-gpi-transfected CHO cells and PMA/ionomycin activated human T cells. CTLA4 was expressed on CHO and COS cells by linking the extracellular domain of CTLA4 to a glycophosphatidylinositol (gpi) anchor. DNA encoding the extracellular domain of CTLA4 was amplified from a human CTLA4 cDNA by PCR using as sense primer, CATGAAGCTTCTCGAGCCGCCACCATG-GCTTGCCTTGGA (SEQ ID NO: 1), containing a Hind III site, a strong translational start site, and the first 15 nucleotides of the CTLA4 coding sequence and an antisense primer, GAGAATTCTAGACTAGCTTAAGTCA-GAATCTGGGCACGGT (SEQ ID NO: 2), containing the last 19 nucleotides of the CTLA4 extracellular domain and an Afl II site. PCR conditions were 94°, 1 min, 43°, 1 min, 72°, 1 min for 35 cycles followed by one cycle of 72° for 10 min. The PCR product was digested with Hind III and Afl II, gel purified, and ligated into a Hind III and Afl II digested pCDM8 vector containing the gpi anchor of human CD58 (see *J. Immunol.* 148:3271, kindly provided by Dr. Donald Staunton, Center for Blood Research, Boston, Mass.). Plasmid containing the CTLA4-gpi insert were transiently transfected into COS cells and strongly expressed cell surface CTLA4, as judged by binding of B7-Ig fusion protein. The CTLA4-gpi plasmid was cotransfected into CHO cells with a plasmid encoding neomycin resistance and stable transfectants were selected with G418. CHO cell transfectants were sorted on the basis of B7-Ig binding and cloned.

Cells for flow cytometry (either CHO-CTLA4 or activated human T cells) were washed thoroughly in 1% BSA in phosphate-buffered saline, pH 7.2, then incubated with 50 µl hybridoma supernatant or culture media per $10^6$ cells for 30 minutes at 4° C. Following the incubation, the cells were washed 3× with 1% BSA in phosphate-buffered saline, pH 7.2, then incubated in 50 µl of a 1:40 dilution of fluorescein conjugated Goat anti-Mouse IgG (H&L) antibodies (Zymed Laboratories, San Francisco, Calif.) for 30 minutes at 4° C. The cells were then washed 3× in 1% BSA in phosphate-buffered saline, pH 7.2 and fixed in 1% paraformaldehyde solution. The cell samples were then analyzed on a FACScan flow cytometer (Becton Dickinson, San Jose, Calif.).

Primary and secondary screening of anti-CTLA4 monoclonal antibodies as described above led to the isolation of five mAbs for further characterization: ER4.7G11 (referred to as 7G 1), ER5.3D8 (referred to as 3D8), ER5.4D3 (referred to as 4D3), ES5.3D6 (referred to as 3D6) and ES5.4E3 (referred to as 4E3). The ER series of antibodies were raised against recombinant human CTLA4, whereas the ES series of antibodies were raised against activated human T cells.

EXAMPLE 2

Characterization of Anti-CTLA4 Monoclonal Antibodies

Binding Specificity

To determine the binding specificity of the five mAbs, 7G11, 4D3, 3D6, 3D8 and 4E3, their binding to either CHO cells transfected to express CD28 or CHO cells transfected to express CTLA4 was assessed by indirect immunofluorescence. The binding pattern of the different anti-CTLA4 mAbs (compared to the control anti-CD28 mAb 3D10) is summarized below in Table 1:

TABLE 1

| Antibody | Clone | Isotype | Binding to CHO-CD28 | Binding to CHO-CTLA4 |
|---|---|---|---|---|
| anti-CD28 | 3D10 | IgG2a | + | − |
| anti-CD28/CTLA4 | 7G11 | IgG2a | + | + |
| anti-CTLA4.1 | 4D3 | IgG2b | − | + |
| anti-CTLA4.2 | 3D6 | IgG1 | − | + |
| anti-CTLA4.3 | 3D8 | IgG2b | − | + |
| anti-CTLA4.4 | 4E3 | IgG2b | − | + |

The 7G11 antibody was found to bind to both CHO-CD28 and CHO-CTLA4 and thus is referred to as an anti-CD28/CTLA4 mAb. In contrast, mAbs 4D3, 3D6, 3D8 and 4E3 were found to bind only the CHO-CTLA4 and thus are CTLA4-specific antibodies. These antibodies are also referred to herein as CTLA4.1, CTLA4.2, CTLA4.3, and CTLA4.4, respectively.

Enitope Mapping

To determine the epitopes recognized by the five mAbs described above, epitope mapping was performed by phage display library (PDL) screening and was confirmed using synthetic peptides. A random 20 amino acid PDL was prepared by cloning a degenerate oligonucleotide into the fUSE5 vector (Scott, J. K. and Smith, G. P. (1990) *Science* 249:386-390) as described in Cwirla, S. E. et al. (1990) *Proc. Natl. Acad. Sci. USA* 87:6378-6382. The PDL was used to identify short peptides that specifically bound mAbs anti-CD28/CTLA4 and anti-CTLA4.1-CTLA4.4 by a micropanning technique described in Jellis, C. L. et al. (1993) *Gene* 137: 63-68. Individual phage clones were purified from the library by virtue of their affinity for immobilized mAb and the random peptide was identified by DNA sequencing.

Sequence analysis of twenty clones selected from panning with anti-CD28/CTLA4 (7G11) yielded the nine unique peptide sequences shown below.

mAb 7G11 Selected Phage Peptides

| | |
|---|---|
| RYLT[PPTTL]SRPVSQNSART | (SEQ ID NO: 3) |
| RDVTLA[APFFI]GGPPATVHT | (SEQ ID NO: 4) |
| DEVSAASW[PPYYI]WERVPHA | (SEQ ID NO: 5) |
| LRPTHQFL[PAYYL]SNRQLSL | (SEQ ID NO: 6) |
| HFDYMIRNR[TPYYQ]WPTVGQ | (SEQ ID NO: 7) |
| RDRTGAVVGTQ[PPYWL]GAFR | (SEQ ID NO: 8) |
| GFWGMEHNLTTGLS[PTWYL]K | (SEQ ID NO: 9) |
| SWNLRSLPDQPIGSP[PPYWL] | (SEQ ID NO: 10) |
| FAFKLGGNGLGGATY[PPYFI] | (SEQ ID NO: 11) |

From these nine peptides, a consensus binding sequence of five residues, P-P-Y-Y-L/I (SEQ ID NO: 12) was identified, within which aromatic residues F and W were frequently substituted for Y. The sequence P-P-Y-Y-L (SEQ ID NO: 13) was identified within the extracellular domain of hCTLA4, within or very close to the CDR3 domain, a portion of which is encompassed in the CTLA4 synthetic peptide RP 454:

| | |
|---|---|
| RP 454: KVELMYP[PPYYL]GIGNGTGG | (SEQ ID NO: 14) |

The peptide RP 454 was used to confirm the epitope of anti-CD28/CTLA4 and could compete with native hCTLA4 for binding of anti-CD28/CTLA4. The sequence identity of CD28 and CTLA4 across the mapped region explains the observed cross reactivity with this mAb on CHO-CD28 and CHO-CTLA4.

MAbs CTLA4.1-CTLA4.4 were panned separately and it was discovered that phage from any of these individual pannings would react specifically to any of the four mAbs. DNA sequence analysis of forty-two phage clones yielded the fourteen peptides shown below:

mAbs 4D3, 3D6, 3D8 and 4E3 Selected Phase Peptides

| | |
|---|---|
| GGLVMIERFNKLE[LTWADD]D | (SEQ ID NO: 15) |
| VCALPDVGYEF[LTSNAD]EPC | (SEQ ID NO: 16) |
| YLANHFGWTS[MVWDAD]DTGH | (SEQ ID NO: 17) |
| RNWARRTSN[LSWDGD]DGSRG | (SEQ ID NO: 18) |
| TAERCVS[LTWNDD]TCDLTGA | (SEQ ID NO: 19) |
| FGLQS[LCWEED]AGLVFGQDS | (SEQ ID NO: 20) |
| NKES[LNWADE]LVRKDPPHGV | (SEQ ID NO: 21) |
| YTE[LTFAND]GLGSGKNLIPK | (SEQ ID NO: 22) |
| YGA[LTCFND]RSDCFFTSPFI | (SEQ ID NO: 23) |
| QS[LTFEDD]GSSFLIYRATSD | (SEQ ID NO: 24) |
| H[LNWGEE]VRHQGEPRADQPF | (SEQ ID NO: 25) |
| V[LTFLER]LLPAVVPRSCHPG | (SEQ ID NO: 26) |
| [LSWGLE]PWEGSFLWLTESPM | (SEQ ID NO: 27) |
| [LNWDID]SMPMGVYCDVPDSC | (SEQ ID NO: 28) |

From these peptides, the shared epitope was mapped to a stretch of six residues on hCTLA4 having the amino acid sequence L-T-F-L-D-D (SEQ ID NO: 29). This epitope is located in the CDR2-like region of CTLA4 and is distinct from the P-P-Y-Y-L (SEQ ID NO: 13) region described above as the epitope for the anti-CD28/CTLA4 mAb. The shared anti-CTLA4.1-CTLA4.4 epitope is contained within the synthetic CTLA4 peptide RP 365:

| | |
|---|---|
| RP 365: AATYMMGNE[LTFLDD]SIC | (SEQ ID NO: 30) | which was used to confirm the epitope mapping results.

Cross-Competition with B7-1 and B7-2

Since the 5 anti-CTLA4 mAbs bound to two distinct antigenic regions on the CTLA4 molecule, it was determined whether either of these regions was part of the binding site for family members. Monoclonal antibodies 7G11 and 4D3 were tested for their ability to block the binding of B7-1-Ig to CTLA4-Ig (constructed as described in Linsley, P. S. et al. (1991) *J. Exp. Med.* 173:721-730; and Linsley, P. S. et al. (1991) *J. Exp. Med.* 174:561-569) using the following experimental formats:

A Nunc Maxisorp plate was coated overnight at room temperature with a solution of 20 μg/ml of CTLA4-Ig in PBS, then blocked for 1 hour with PBS/1% BSA. 10 μg/ml of biotinylated B7-1-Ig was added with increasing amounts of monoclonal antibodies, up to 100 μg/ml. Control reagents ("cold" B7-1-Ig, CTLA4-Ig, anti-B7-1 antibodies 4B2 and 6B10, and anti HIV-antibody 59.1) were also tested. The biotinylated B7-1-Ig was visualized using strepavidin-horse radish peroxidase (HRP) and enzymatic substrate. The results, summarized below, show that 7G11 and 4D3 were ineffective competitors:

TABLE 2

Standard curve for binding biotinylated B7-1-Ig to CTLA4-Ig:

| amount of biotinylated B701-Ig | OD |
|---|---|
| 20 ugs/ml | 1.0 |
| 10 | 1.1 |
| 5 | 1.2 |
| 2.5 | 1.1 |
| 1.25 | 0.84 |
| 0.6 | 0.43 |

TABLE 3

Effect of various competitors on the binding of 10 μg/ml of biotinylated B7-1-Ig to immobilized CTLA4-Ig:

| amount of | OD. with competitor | | | | | | |
|---|---|---|---|---|---|---|---|
| competitor | 7G11 | 4D3 | 4B2U | 6B10 | 59.1 | B7-1-Ig | CTLA4-Ig |
| 100 μg/ml | 1.1 | 1.2 | 0.25 | 0.14 | 1.6 | 0.17 | 0.24 |
| 25 | 1.2 | 1.3 | 0.63 | 0.28 | 1.4 | 0.66 | 0.86 |
| 6.25 | 1.2 | 1.3 | 1.2 | 1.0 | 1.5 | 1.2 | 1.3 |
| 1.5 | 1.2 | 1.3 | 1.9 | 1.8 | 1.6 | 1.5 | 1.6 |

In the second experiment the format was "flipped". The plate was coated overnight with 20 μg/ml of B7-1-Ig in PBS, blocked with PBS/1% BSA, then incubated with biotinylated CTLA4-Ig plus various competitors and controls as delineated for the first experiment. The biotinylated CTLA4-Ig was visualized using strepavidin:HRP and enzymatic substrate. The results were similar to those shown above:

TABLE 4

Standard curve for binding biotinylated CTLA4-Ig to B7-1-Ig:

| amount of biotinylated CTLA4-Ig | OD |
|---|---|
| 200 μg/ml | 1.4 |
| 100 | 1.4 |
| 50 | 1.0 |
| 25 | 0.53 |
| 12.5 | 0.30 |
| 6.25 | 0.16 |

TABLE 5

Effect of various competitors on the binding of biotinylated CTLA4-Ig to immobilized B7-1-Ig:

| amount of | OD. with competitor | | | | | | |
|---|---|---|---|---|---|---|---|
| competitor | 7G11 | 4D3 | 4B2 | 6B10 | 59.1 | B7-1-Ig | CTLA4-Ig |
| 100 μg/ml | 1.4 | 1.3 | 0.06 | 0.06 | 1.3 | 0.06 | 0.24 |
| 25 | 1.4 | 1.3 | 0.07 | 0.07 | 1.3 | 0.09 | 0.49 |
| 6.25 | 1.4 | 1.3 | 0.09 | 0.10 | 1.3 | 0.12 | 0.68 |
| 1.5 | 1.4 | 1.3 | 0.22 | 0.25 | 1.3 | 0.27 | 1.1 |

Taken together these complementary data sets indicate that the mAbs 7G11 and 4D3 do not have the capacity to disrupt the binding of CTLA4-Ig to B7-1-Ig. Similar results were observed in experiments using B7-2-Ig. The result that the anti-CD28/CTLA4 antibody (7G11) did not inhibit the binding of B7-1-Ig to CTLA4 (or vice versa) was surprising since it had previously been suggested that the sequence M-Y-P-P-P-Y (SEQ ID NO: 31), which overlaps with the P-P-Y-Y-L (SEQ ID NO: 13) epitope mapped for the 7G11 antibody, was part of the binding site of both CD28 and CTLA4 to B7-1 (see Harper, K. et al. (1991) *J. Immunol.* 147:1037-1044).

EXAMPLE 3

Induction of Apoptosis in T Cells by Anti-CTLA4 Antibodies

In this example, apoptosis was induced in previously activated T cells by ligation of CTLA4 on the T cell surface using an anti-CTLA4 mAb. In the first series of experiments, an alloreactive T cell clone was used. Alloreactive T cell clones with specificity for HLA-DR7 were made from HLA-DR7 negative individuals. T cell clones were activated by culture for 24 hr with an irradiated DR7$^+$ homozygous lymphoblastoid cell line (LBL-DR7) which induces CTLA4 surface expression by 24 hrs. T cells were cultured at a concentration of $10^5$ cells/well in 96-well flat-bottomed microtiter plates at 37° C., 5% $CO_2$. Activated T cell clones were rechallenged with NIH-3T3 cells transfected with human DRα and DR7β (t-DR7; described in Gimmi, C. D. et al. (1993) *Proc. Natl. Acad. Sci. USA* 90:6586-6590) alone or together with anti-CD28 or anti-CTLA4 mAbs to provide a second signal. Thymidine incorporation, as an index of mitotic activity, was assessed by standard techniques. IL-2 and IL-4 concentrations in culture supernatants were assayed by standard ELISA. Apoptosis was assessed by the presence of DNA fragmentation on agarose gel electrophoresis as described in Quingsheng, T. et al. (1991) *Cell* 67:629-639. Briefly, DNA was extracted from cells and the samples were loaded onto a 1% agarose gel containing 0.5 μg/ml ethidium bromide. After electrophoresis, DNA was visualized under UV light and assessed for the presence of nucleosomal length fragments characteristic of apoptosis. and Additionally, apoptosis was assessed by uptake of Hoechst 33342 dye as described in Hardin, J. A. (1992) *J. Immunol. Methods* 154:99-107.

The results are illustrated graphically in FIG. 1A. Activated T cell clones proliferated in response to challenge with t-DR7 without detectable IL-2 accumulation. The addition of anti-CD28 or anti-CD28/CTLA4 mAb (e.g., 7G11) resulted in significant proliferation and IL-2 accumulation. In contrast, the addition of anti-CTLA4.1 mAb to the t-DR7 stimulated T cell culture did not stimulate proliferation, but instead resulted in significantly decreased proliferation, no detectable IL-2 accumulation, and induced apoptosis as measured by DNA fragmentation. The addition of exogenous IL-2 to the t-DR7 and CTLA4.1 mAb stimulated T cell culture resulted in significant T cell proliferation comparable to that observed with the addition of IL-2 alone to t-DR7 and prevented the induction of apoptosis by t-DR7 and anti-CTLA4 mAb. Following CTLA4 ligation with CTLA4.1, activated T cell clones were not observed to proliferate in the presence of exogenous IL-2, which is consistent with the conclusion that these cells underwent antigen specific clonal deletion.

In a second series of experiments, it was determined whether CTLA4 ligation could also induce apoptosis in previously activated normal human T cells. CD4 positive T cell blasts were isolated by negative depletion after culture of PBMC for four days in media containing phytohemagglutinin (PHA) to activate the T cells. Cells were washed extensively and then rechallenged with anti-CD3 mAb in the presence of various second signals.

Figure 2A:
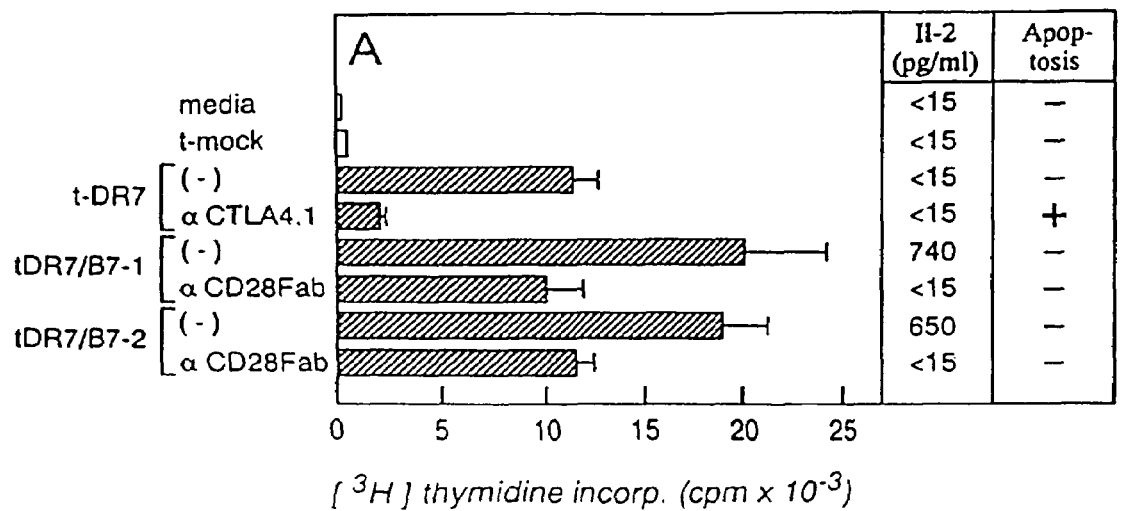
FIG. 2A is a graphic representation of T cell responses (proliferation, IL-2 production or apoptosis) by activated DR7-specific T cell clones upon rechallenge with cells expressing antigen alone (t-DR7) or cells expressing both antigen and either B7-1 (tDR7/B7-1) or B7-2 (tDR7/B7-2), demonstrating that neither B7-1 nor B7-2 induces antigen specific apoptosis.
Figure 2B:
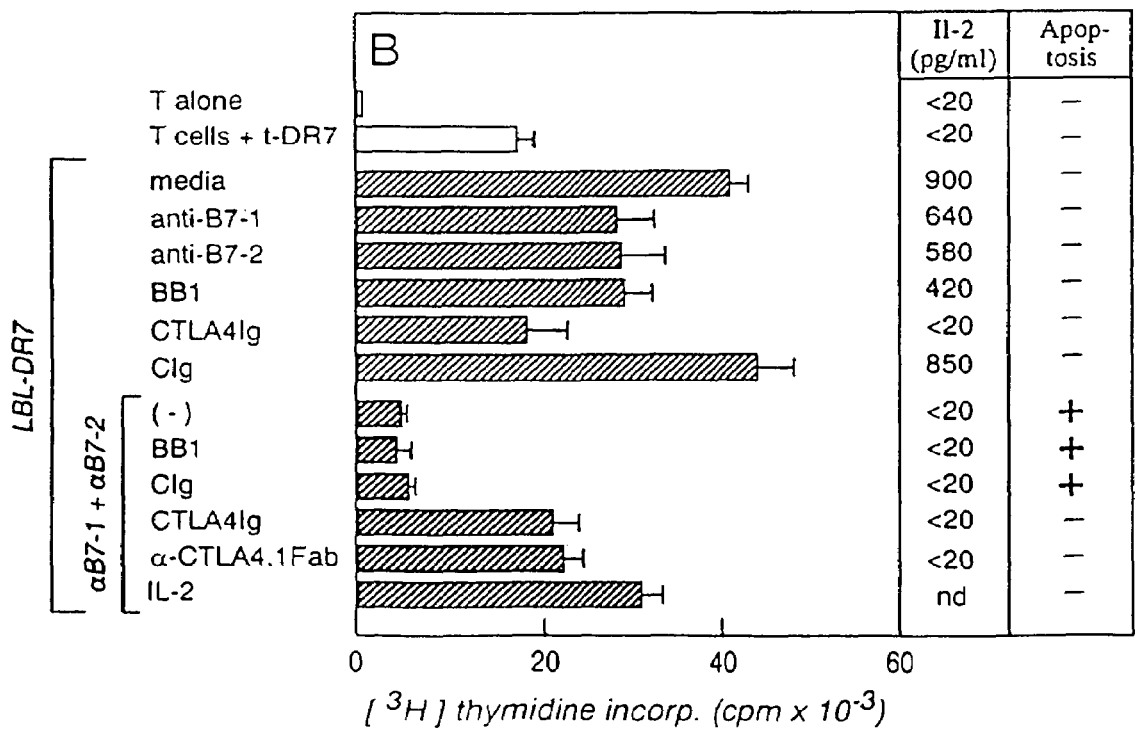
FIG. 2B is a graphic representation of T cell responses (proliferation, IL-2 production or apoptosis) by activated DR7-specific T cell clones upon rechallenge with the indicated cells together with the indicated mAbs or fusion proteins, demonstrating that antigen specific apoptosis is induced by a non-B7-1, non-B7-2 CTLA4 binding ligand.

The results are illustrated graphically in FIG. 2B. Anti-CTLA4 mAbs in the absence of anti-CD3 treatment had no effect on T cell proliferation or IL-2 production. Anti-CD3 alone induced modest proliferation of PHA blasts accompanied by low levels of IL-2 accumulation. The addition of anti-CD28 or anti-CD28/CTLA4 (e.g., 7G11) mAbs enhanced both proliferation and IL-2 accumulation. Similar to the results described above for the HLA-DR7 specific alloreactive T cell clone, anti-CD3 stimulation of activated normal peripheral blood T cells in the presence of any of the anti-CTLA4 mAbs (e.g., CTLA4.1-CTLA4.4) resulted in decreased proliferation, absence of IL-2 accumulation, and apoptosis. Apoptosis was detectable as early as 6 hrs of culture. Cross-linking of CTLA4 was necessary since anti-CTLA4.1 Fab had no effect. As observed for the activated T cell clones, the addition of exogenous IL-2 to anti-CTLA4.1 mAb protected against apoptosis. Similarly, the addition of anti-CD28 also protected against apoptosis. The apoptosis did not appear to be merely as a result of loss of production of IL-2 since CD4$^+$ PHA blasts cultured in media alone for periods up to 24 hours did not undergo apoptosis. The specificity of CTLA4 cross-linking was provided by the finding that anti-CD45, anti-CD45RA, anti-CD45RO, anti-CD4, anti-CD5 or anti-CD6 mAb cross-linking, under identical culture conditions, did not induce decreased proliferation or apoptosis in any of 5 experiments performed. Similar levels of apoptosis were also observed in isolated unfractionated T cells, CD28 positive and CD8 positive PHA blasts examined under the identical culture conditions.

EXAMPLE 4

Induction of Apoptosis in T Cells by a Novel CTLA4 Ligand

As described in Example 2, ligation of CTLA4 with an anti-CTLA4 antibody, in the presence of a primary activation signal, induced apoptosis on previously activated normal T cells and alloreactive T cell clones. It was next determined whether either of the known CTLA4 ligands, B7-1 or B7-2, could also mediate this function. Using the identical system of T cell activation described above, activated alloreactive T cell clones were rechallenged with COS cells transfected to express HLA-DR7 alone (t-DR7) alone or COS cells transfected to coexpress both HLA-DR7 and either B7-1(tDR7/B7-1) or B7-2 (tDR7/B7-2) to provide signal 2. Control mock transfected cells (t-mock) were transfected with the pCDNAI plasmid alone. The results are illustrated graphically in FIG. 2A. As previously observed, culture of activated T cell clones with t-DR7 in the presence of anti-CTLA4.1 suppressed proliferation and induced apoptosis. In contrast, both t-DR7/B7-1 and t-DR7/B7-2 induced augmented proliferation and did not induce apoptosis. Addition of anti-CD28 Fab blocked the augmented proliferation induced by both B7-1 and B7-2 (i.e., the level of proliferation was reduced to that observed with t-DR7 alone) demonstrating that the proliferative signal provided by B7-1 or B7-2 was indeed mediated via CD28. Moreover, under these circumstances where B7-1 or B7-2 binds to CTLA4 in the absence of CD28-mediated signaling, there was neither decreased proliferation nor apoptosis as compared to t-DR7 alone. Identical results were observed with PHA activated normal human T cells. From these experiments, it can be concluded that neither of the molecularly cloned CTLA4 natural ligands (i.e., B7-1 or B7-2) mediate antigen specific clonal deletion of T cells.

Considering that the two molecularly cloned CTLA4 natural ligands did not mediate antigen specific clonal deletion, it was next determined whether an alternative CTLA4 ligand mediated apoptosis. Activated alloreactive T cell clones were rechallenged with LBL-DR7 alone or in the presence of various mAbs and Ig fusion proteins as shown in FIG. 2B, which illustrates the results of the experiments. All mAbs were added to the culture at a final concentration of 10 μg/ml. Blocking mAbs directed against B7-1, B7-2, and B7-3 (BB1 mAb) individually suppressed LBL-DR7 induced proliferation by 25%. Addition of CTLA4-Ig but not control Ig suppressed proliferation by 50% and totally blocked IL-2 production. The resulting proliferation was comparable to that observed with t-DR7 alone. However, the combined addition of anti-B7-1 and anti-B7-2 mAbs markedly suppressed proliferation and, more importantly, T cells underwent apoptosis. Further addition of BB1 mAb or control Ig to anti-B7-1 and anti-B7-2 mAbs had no additional effects on either proliferation or apoptosis. In contrast, the addition of either CTLA4-Ig or CTLA4.1 Fab to anti-B7-1 and anti-B7-2 mAbs completely blocked apoptosis and returned the level of proliferation to that observed with t-DR7 alone. These data demonstrate that the ligand expressed on LBL-DR7 that induced apoptosis is not B7-1 nor B7-2 but is a CTLA4 binding ligand that signals through CTLA4. Apoptosis was antigen specific since LBL-DR1 cells under identical culture conditions did not decrease proliferation or induce apoptosis. Similar to previous observations described in Example 4, addition of IL-2 to anti-B7-1 and anti-B7-2 abrogated the suppression of proliferation and apoptosis. Identical results were again observed with PHA blasts.

Taken together, these results demonstrate that the physiologic ligand for CTLA4 that mediates antigen specific T cell apoptosis is: 1) expressed on LBL-DR7 cells, 2) neither B7-1 nor B7-2 since blocking B7-1 and B7-2 did not inhibit apoptosis, 3) a CTLA4 binding ligand since CTLA4Ig blocked apoptosis, and 4) signals through CTLA4 since anti-CTLA4.1 also blocked apoptosis. Moreover, the functional epitope on this natural ligand is likely to bind to the identical CTLA4 epitope (L-T-F-L-D-D; SEQ ID NO: 29) recognized by all four anti-CTLA4 mAbs described herein since CTLA4.1 Fab could block apoptosis. These results are consistent with the hypothesis that CTLA4 is not a redundant CD28-like costimulatory pathway but rather a distinct signaling pathway capable, under appropriate conditions, of clonally deleting previously activated T cells and furthermore, that a novel natural CTLA4 ligand present on LBL-DR7 can mediate this apoptosis.

During an ongoing immune response, there is a balance between signals that mediate activation/amplification and those that subsequently induce antigen specific cellular deletion. Either cross-linking of CD28 or the common binding region of CD28/CTLA4 by mAbs or their natural ligands B7-1 or B7-2 provides such a positive costimulatory signal resulting in IL-2 accumulation. The results described herein suggest that signals which induce IL-2 accumulation are dominant since they amplify the immune response and thereby protect the ongoing immune response from CTLA4 mediated apoptosis. Since B7-1 and B7-2 are ligands for both CD28 and CTLA4, in most instances, they should mediate an amplification signal rather than cellular depletion. During this interval, crosslinking of CTLA4 does not mediate apoptosis, but in contrast, can provide a synergistic costimulatory signal to CD28. Following T cell activation, CD28 engagement by B7-1 downregulates CD28 synthesis and function (Linsley, P. S. et al. (1993) *J. Immunol.* 150:3161-3169) as CTLA4 expression increases. Under conditions when the proliferative response is waning, crosslinking of CTLA4 in the absence of CD28 mediated costimulation can then induce cellular deletion of previously activated cells. This functional capacity to either costimulate or induce apoptosis depending upon the state of activation of the T cell is reminiscent of the functional repertoire of members of the TNF family of receptors (see Smith, C. A. et al. (1994) *Cell* 76:959-962). However, unlike apoptosis induced by members of the TNF receptor family, CTLA4 crosslinking mediates antigen specific clonal deletion since it also requires a signal through the TCR.

EXAMPLE 5

Cloning of a CTLA4 Ligand that Induces Apoptosis in Activated T Cells

The natural CTLA4 ligand which mediates apoptosis in T cells is molecularly isolated by expression cloning based upon its interaction with CTLA4. As demonstrated in Example 5, the natural CTLA4 ligand is expressed on the surface of a B lymphoblastoid cell line (LBL). Such LBL cell lines are known in the art and can be constructed by standard techniques involving Epstein-Barr virus transformation of B lymphoma cells. To isolate the natural CTLA4 ligand mediating apoptosis in T cells, a cDNA expression library is prepared from such an LBL cell line as follows:

A. Construction of a cDNA Expression Library

A cDNA library is constructed in a eukaryotic expression vector such as the pCDM8 vector (Seed, (1987) *Nature* 329: 840) using poly (A)$^+$ RNA isolated from the LBL cell line as described (Aruffo et al. (1987) *Proc. Natl. Acad. Sci. USA* 84:3365). To prepare total RNA, LBL cells are harvested from culture and the cell pellet is homogenized in a solution of 4 M guanidine thiocyanate, 0.5% sarkosyl, 25 mM EDTA, pH 7.5, 0.13% Sigma anti-foam A, and 0.7% mercaptoethanol. RNA is purified from the homogenate by centrifugation for 24 hour at 32,000 rpm through a solution of 5.7 M CsCl, 10 mM EDTA, 25 mM Na acetate, pH 7. The pellet of RNA is dissolved in 5% sarkosyl, 1 mM EDTA, 10 mM Tris, pH 7.5 and extracted with two volumes of 50% phenol, 49% chloroform, 1% isoamyl alcohol. RNA is ethanol precipitated twice. Poly (A)$^+$ RNA used in cDNA library construction is purified by two cycles of oligo (dT)-cellulose selection.

Complementary DNA is synthesized from 5.5 µg of poly (A)$^+$ RNA in a reaction containing 50 mM Tris, pH 8.3, 75 mM KCl, 3 mM MgCl$_2$, 10 mM dithiothreitol, 500 µM dATP, dCTP, dGTP, dTTP, 50 µg/ml oligo(dT)$_{12-18}$, 180 units/ml RNasin, and 10,000 units/ml Moloney-MLV reverse transcriptase in a total volume of 55 µl at 37° C. for 1 hr. Following reverse transcription, the cDNA is converted to double-stranded DNA by adjusting the solution to 25 mM Tris, pH 8.3, 100 mM KCl, 5 mM MgCl$_2$, 250 µM each dATP, dCTP, dGTP, dTTP, 5 mM dithiothreitol, 250 units/ml DNA polymerase I, 8.5 units/ml ribonuclease H and incubating at 16° C. for 2 hr. EDTA is added to 18 mM and the solution is extracted with an equal volume of 50% phenol, 49% chloroform, 1% isoamyl alcohol. DNA is precipitated with two volumes of ethanol in the presence of 2.5 M ammonium acetate and with 4 micrograms of linear polyacrylamide as carrier. In addition, cDNA is synthesized from 4 µg of poly(A)$^+$ RNA in a reaction containing 50 mM Tris, pH 8.8, 50 µg/ml oligo(dT)$_{12-18}$, 327 units/ml RNasin, and 952 units/ml AMV reverse transcriptase in a total volume of 100 µl at 42° C. for 0.67 hr. Following reverse transcription, the reverse transcriptase is inactivated by heating at 70° C. for 10 min. The cDNA is converted to double-stranded DNA by adding 320 µl H$_2$O and 80 µl of a solution of 0.1M Tris, pH 7.5, 25 mM MgCl$_2$, 0.5 M KCl, 250 µg/ml bovine serum albumin, and 50 mM dithiothreitol, and adjusting the solution to 200 µM each dATP, dCTP, dGTP, dTTP, 50 units/ml DNA polymerase I, 8 units/ml ribonuclease H and incubating at 16° C. for 2 hours. EDTA is added to 18 mM and the solution is extracted with an equal volume of 50% phenol, 49% chloroform, 1% isoamyl alcohol. DNA is precipitated with two volumes of ethanol in the presence of 2.5 M ammonium acetate and with 4 micrograms of linear polyacrylamide as carrier.

The DNA from 4 µg of AMV reverse transcription and 2.0 µg of Moloney MLV reverse transcription are combined. Non-selfcomplementary BstXI adaptors are added to the DNA as follows: The double-stranded cDNA from 6 µg of poly(A)$^+$ RNA is incubated with 3.6 µg of a kinased oligonucleotide of the sequence CTTTAGAGCACA (SEQ ID NO:31) and 2.4 µg of a kinased oligonucleotide of the sequence CTCTAAAG (SEQ ID NO:32) in a solution containing 6 mM Tris, pH 7.5, 6 mM MgCl$_2$, 5 mM NaCl, 350 µg/ml bovine serum albumin, 7 mM mercaptoethanol, 0.1 mM ATP, 2 mM dithiothreitol, 1 mM spermidine, and 600 units T4 DNA ligase in a total volume of 0.45 ml at 15° C. for 16 hours. EDTA is added to 34 mM and the solution is extracted with an equal volume of 50% phenol, 49% chloroform, 1% isoamyl alcohol. DNA is precipitated with two volumes of ethanol in the presence of 2.5 M ammonium acetate.

DNA larger than 600 bp is selected as follows: The adaptored DNA is redissolved in 10 mM Tris, pH 8, 1 mM EDTA, 600 mM NaCl, 0.1% sarkosyl and chromatographed on a Sepharose CL-4B column in the same buffer. DNA in the void volume of the column (containing DNA greater than 600 bp) is pooled and ethanol precipitated.

The pCDM8 vector is prepared for cDNA cloning by digestion with BstXI and purification on an agarose gel. Adaptored cDNA from 6 µg of poly(A)$^+$ RNA is ligated to 2.25 µg of BstXI cut pCDM8 in a solution containing 6 mM Tris, pH 7.5, 6 mM MgCl$_2$, 5 mM NaCl, 350 µg/ml bovine serum albumin, 7 mM mercaptoethanol, 0.1 mM ATP, 2 mM dithiothreitol, 1 mM spermidine, and 600 units T4 DNA ligase in a total volume of 1.5 ml at 15° C. for 24 hr. The ligation reaction mixture is then transformed into competent *E.coli* DH10B/P3 by standard techniques.

Plasmid DNA is prepared from a 500 ml culture of the original transformation of the cDNA library. Plasmid DNA is purified by the alkaline lysis procedure followed by twice banding in CsCl equilibrium gradients (Maniatis et al, *Molecular Cloning: A Laboratory Manual*, Cold Spring Harbor, N.Y. (1987)).

B. Cloning Procedure

In the cloning procedure, the cDNA expression library is introduced into a eukaryotic cell line such as COS cells and the cells are screened with CTLA4 protein (e.g., a CTLA4Ig fusion protein) to identify transfectants expressing a CTLA4 ligand on their surface. Since in addition to containing cDNA encoding the CTLA4 ligand which induces apoptosis, the cDNA library is likely to also contain "contaminating" B7-1 and B7-2 cDNA, the second and third rounds of library screening include a pretreatment with anti-B7-1 and anti-B7-2 antibodies, followed by immunomagnetic bead depletion using anti-mouse Ig-coupled magnetic beads to remove clones expressing these proteins. In the first round of screening, thirty 100 mm dishes of 50% confluent COS cells are transfected with 0.05 µg/ml LBL cell line library DNA using the DEAE-Dextran method (Seed, B. et al. (1987) *Proc. Natl. Acad. Sci. USA* 84:3365). The cells are trypsinized and replated after 24 hours. After 47 hours, the cells are detached by incubation in PBS/0.5 mM EDTA, pH 7.4/0.02% Na azide at 37° C. for 30 min.

Detached cells are treated with 10 µg/ml CTLA4Ig (recombinant CTLA4-human Ig fusion protein is described in Linsley, P. S. et al. (1991) *J. Exp. Med.* 174:561-569; and Gimmi, C. D. et al. (1993) *Proc. Natl. Acad. Sci. USA* 90:6586-6590).

Cells are incubated with the fusion protein for 45 minutes at 4° C. Cells are washed and distributed into panning dishes coated with affinity-purified goat anti-human IgG antibody and allowed to attach at room temperature. After 3 hours, the plates are gently washed twice with PBS/0.5 mM EDTA, pH 7.4/0.02% Na azide, 5% FCS and once with 0.15 M NaCl, 0.01 M Hepes, pH 7.4, 5% FCS. Unbound cells are thus removed and episomal DNA is recovered from the adherent panned cells (i.e., cells which bind to CTLA4Ig) by conventional techniques.

Episomal DNA is transformed into E. coli DH10B/P3. The plasmid DNA is re-introduced into COS cells via spheroplast fusion as described (Seed, B. et al. (1987) Proc. Natl. Acad. Sci. USA 84:3365) and the cycle of expression and panning is repeated twice. In the second and third rounds of selection, after 47 hours, the detached COS cells are first incubated with 10 µg/ml murine anti-B7-1 mAb (e.g., mAb 133, described in Freedman, A. S. et al. (1987) J. Immunol. 137:3260-3267, mAb L307, commercially available from Becton Dickinson, and/or B 1.1, from Repligen Corp.) and anti-B7-2 mAb (e.g., mAb B-70, described in Azuma, M. et al. (1993) Nature 366:76-79, commercially available from Pharmingen) for 45 minutes at 4° C. Cells expressing B7-1 or B7-2 are removed using anti-mouse IgG and IgM coated magnetic beads. COS cells are then treated with 10 µg/ml of human CTLA4Ig (hCTLA4Ig). Cells expressing a novel CTLA4 ligand are selected by panning on dishes coated with goat anti-human IgG antibody. After the third round of screening, plasmid DNA is prepared from individual colonies and transfected into COS cells by the DEAE-Dextran method. Expression of CTLA4 ligand on transfected COS cells is analyzed by indirect immunofluorescence with CTLA4Ig.

In an alternative approach, clones are selected based upon binding to the BB1 antibody. One candidate for the novel CTLA4 ligand is B7-3, which is defined by the binding of the BB1 mAb (Boussiotis, V. A. et al. (1993) Proc. Natl. Acad. Sci. USA 90:11059-11063). Although, the BB1 mAb was unable to block CTLA4 mediated apoptosis (see Example 5), it is possible that B7-3 is the CTLA4 ligand which mediates apoptosis but that the BB1 mAb is not a blocking antibody for this function. Accordingly, a cDNA expression library can be screened, as described above, for clones which bind to the BB1 mAb (the BB1 mAb is described in Yokochi, T. et al. (1982) J. Immunol. 128:823-827). Clones are isolated by panning on plates coated with goat anti-mouse IgM secondary antibody. The LBL cDNA library can be used or, alternatively, a library can be prepared from activated human keratinocytes, which are known to express the BB1 antigen, and screened as described above.

The ability of a CTLA4 ligand, isolated by expression cloning as described above, to induce antigen specific apoptosis in activated T cells can be assessed using the system described in the previous examples. For example, a cDNA isolated from the library screening can be introduced into CHO cells to create CHO transfectants expressing the CTLA4 ligand on their surface (CHO-CTLA4L). To assess apoptosis in normal human T cells, PHA-activated CD4+ T cell blasts are cultured with anti-CD3 and CHO-CTLA4L and DNA fragmentation is determined as a measure of apoptosis. To assess antigen specific apoptosis in alloreactive T cells, a previously activated HLA-DR7-specific T cell clone is cultured with CHO cells transfected to express both HLA-DR7 and the CTLA4 ligand (CHO-DR7/CTLA4L) and DNA fragmentation and down-regulation of T cell proliferation are assessed as a measure of apoptosis and biological function.

EXAMPLE 6

Expression of Human CTLA4 Extracellular Domain in E. coli

Cloning of CTLA4 Extracellular Domain

The extracellular domain of CTLA4 was expressed in E. coli after cloning into expression vector pETCm11a. This vector was derived from expression vector pET-11a (Novagen Inc., Madison Wis.) by cloning a chloramphenicol resistance gene cassette into the ScaI restriction site within the ampicillin resistance gene. The extracellular domain of CTLA4 was prepared from plasmid phCTLA4 by PCR amplification using oligonucleotide 5'GCAGAGAGA-CATATGGCAATGCACGTGGCCCAGCCTGCTGTGG-3' (SEQ ID NO: 37) as forward primer and oligonucleotide 5'-GCAGAGAGAGGATCCTCAGTCAGTTAGT-CAGAATCTGGGCACGGTTCTGG-3' (SEQ ID NO: 38) as reverse primer. The forward PCR primer contains an NdeI restriction site in which the ATG sequence in the NdeI restriction site is followed immediately by the codon for the first amino acid of mature CTLA4. The reverse PCR primer contains a BamH1 restriction site preceded by translation stop codons in all three reading frames preceded by the last amino acid just prior to the CTLA4 transmembrane domain. PCR amplification with these primer yields a 416 bp fragment bounded by NdeI and BamH1 restriction sites which contains DNA sequences encoding the extracellular domain of CTLA4 preceded by a methionine codon. The PCR product was digested with NdeI plus BamH1 and ligated to expression vector pETCm11a digested with the same restriction enzymes. The ligated DNA was transfected into E. coli strains BL21, HMS 174, RGN714 and RGN715 containing the lambda DE3 helper phage. Transformants were selected in L-agar containing chloramphenicol. Individual transformants were selected and tested for CTLA4 expression after induction by treatment with 0.5 mM IPTG. Whole cell extracts were analyzed on SDS-PAGE gel followed by Coomassie blue staining and western blot analysis. The majority of the CTLA4 protein in these cells was found in inclusion bodies.

Purification of CTLA4 from Inclusion Bodies

Recombinant CTLA4 was recovered from cell pellets by treating the washed cells in lysis buffer (50 mM Tris-HCl pH 8.0, 1 mM PMSF, 5 mM EDTA, 0.5% Triton X-100, and lysozyne at 0.3 mg/ml) followed by sonication. The inclusion bodies were recovered by centrifugation at 20,000×g and solubilized by treatment with solubilization buffer (50 mM Tris-HCl pH8.0, 8 M urea, 50 mM 2-mercaptoethanol (2-ME)). The solubilization was assisted by mixing for two hours at room temperature. The soluble fraction contained CTLA4. The CTLA4 was purified by chromatography on S-sepharose (Pharmacia, Piscataway, N.J.) as follows. The CTLA4 containing supernatant was adjusted to pH 3.4 by the addition of glacial acetic and applied to a S-sepharose column equilibrated in column buffer (100 mM Na-acetate, pH6.5, 8 M urea, 50 mM 2-ME, and 5 mM EDTA). The column was washed with column buffer and the bound CTLA4 eluted with a linear salt gradient (NaCl, 0 to 1 M) prepared in column buffer. Peak fraction exhibiting high $Abs_{280nm}$ values were pooled and dialyzed against dialysis buffer (100 mM Tris-HCl, pH 8.0, 8 M urea, 50 mM, 2-ME, 5 mM EDTA). Remaining contaminating proteins were eliminated by chromatography on a Sephacryl S-100 (Pharmacia, Piscataway, N.J.) sizing column. The resulting preparation was greater than 95% pure CTLA4 as estimated by SDS-PAGE followed by Coomassie blue staining and western blot analysis. Since the estimated size of monomeric recombinant CTLA4 produced in E. coli was approximately 15 kDa, all steps of the purification protocol were tested for the presence of a 15 kDa protein by SDS-PAGE and the presence of CTLA4 verified by western blotting.

Preparation of Secreted CTLA4 from E. coli

A secreted form of CTLA4 was prepared from E. coli as follows. The extracellular domain of CTLA4 was joined to the pelB (Lei. S.-P. et al. (1987) J. Bacteriol. 169: 4379-4383) signal sequence by PCR using plasmid phCTLA4 as template and oligonucleotide 5'GGCACTAGTCATGAAATACCTAT-TGCCTACGGCAGCCGCTGGATTGTTAT-TACTCGCTGCCCAACCAGCGATGGCCG-CAGCAATGCACGTGGCCCAGCCTGCTGTGG3' (SEQ ID NO: 39) as the forward primer and the oligonucleotide of SEQ ID NO: 38, described above, as the reverse primer. The forward PCR primer contains a unique BspH1 restriction site, the complete pelB signal sequence and the 5' end of the extracellular domain of CTLA4. The reverse PCR primer contains a unique BamH1 restriction site preceded by translational stop codons in all three reading frames preceded by the last amino acid before the transmembrane domain of CTLA4. PCR amplification with these primers yielded a 480 by fragment bounded by unique BspH1 and BamH1 restriction sites encoding the pelB signal sequence joined to the CTLA4 extracellular domain. After PCR amplification, the DNA fragment was digested with BspH1 and BamH1 and ligated to expression vector pTrc99A (Pharmacia, Piscataway, N.J.) previously digested with NcoI and BamHI. This resulted in a plasmid which the expression of the pelB-CTLA4 protein was driven by the pTrc promoter present in the pTrc99A expression vector. E. coli host strains transformed with the ligated DNA were selected on L-agar containing ampicillin (50 μg/ml) and individual clones isolated. The expression of CTLA4 in these strains was induced by the treatment of exponentially growing cultures with IPTG (0.5 mM) overnight. Extracts prepared from the culture medium after concentration or by release from periplasm (cells were incubated in 20% sucrose, 10 mM Tris-HCl pH7.5 for 15 minutes at room temperature, collected by centrifugation, and resuspended in water at 4° C. and held on ice for 10 min.) were assayed for the presence of CTLA4 by SDS-PAGE, western blotting and competitive B7 binding ELISA.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. A method for inducing apoptosis in an activated T cell in a subject, comprising administering to the subject an effective amount of an anti-CTLA4 antibody, or fragment thereof, which binds to an epitope on a CTLA4 molecule, said epitope comprising the amino acid sequence $(Xaa)_n$-Leu-Thr-Phe-Leu-Asp-Asp-$(Xaa)_n$ (SEQ ID NO:33), wherein Xaa is any amino acid and n=0-20, and wherein said anti-CTLA4 antibody or fragment thereof stimulates a CTLA4-associated apoptotic signal in the T cell.

2. The method of claim 1, further comprising administering to the subject at least one second agent that inhibits a costimulatory signal in the T cell, wherein the second agent is selected from the group consisting of an anti-CD28 Fab fragment, anti-B7-1 blocking antibodies, anti-B7-2 blocking antibodies, soluble CD28, soluble B7-1, and soluble B7-2.

3. The method of claim 1, wherein the subject suffers from an autoimmune disease.

4. A method for treating a subject suffering from an autoimmune disease, comprising administering to the subject an effective amount of an anti-CTLA4 antibody, or fragment thereof, which binds to an epitope on a CTLA4 molecule, said epitope comprising the amino acid sequence $(Xaa)_n$-Leu-Thr-Phe-Leu-Asp-Asp-$(Xaa)_n$ (SEQ ID NO:33), wherein Xaa is any amino acid and n=0-20.

* * * * *

SEQUENCE LISTING

<160> NUMBER OF SEQ ID NOS: 39

<210> SEQ ID NO 1
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 1
catgaagctt ctcgagccgc caccatggct tgccttgga         39

<210> SEQ ID NO 2
<211> LENGTH: 40
<212> TYPE: DNA
<213> ORGANISM: Artificial Sequence
<220> FEATURE:
<223> OTHER INFORMATION: Synthetic peptide

<400> SEQUENCE: 2
gagaattcta gactagctta agtcagaatc tgggcacggt         40

<210> SEQ ID NO 3
<211> LENGTH: 20
<212> TYPE: PRT
<213> ORGANISM: Artificial Sequence
<220> FEATURE:
<223> OTHER INFORMATION: Synthetic peptide

<400> SEQUENCE: 3

Arg Tyr Leu Thr Pro Pro Thr Thr Leu Ser Arg Pro Val Ser Gln Asn
 1               5                  10                  15

Ser Ala Arg Thr
         20

```
<210> SEQ ID NO 4
<211> LENGTH: 20
<212> TYPE: PRT
<213> ORGANISM: Artificial Sequence
<220> FEATURE:
<223> OTHER INFORMATION: Synthetic peptide

<400> SEQUENCE: 4

Arg Asp Val Thr Leu Ala Ala Pro Phe Phe Ile Gly Gly Pro Pro Ala
 1               5                  10                  15

Thr Val His Thr
        20

<210> SEQ ID NO 5
<211> LENGTH: 20
<212> TYPE: PRT
<213> ORGANISM: Artificial Sequence
<220> FEATURE:
<223> OTHER INFORMATION: Synthetic peptide

<400> SEQUENCE: 5

Asp Glu Val Ser Ala Ala Ser Trp Pro Pro Tyr Tyr Ile Trp Glu Arg
 1               5                  10                  15

Val Pro His Ala
        20

<210> SEQ ID NO 6
<211> LENGTH: 20
<212> TYPE: PRT
<213> ORGANISM: Artificial Sequence
<220> FEATURE:
<223> OTHER INFORMATION: Synthetic peptide

<400> SEQUENCE: 6

Leu Arg Pro Thr His Gln Phe Leu Pro Ala Tyr Tyr Leu Ser Asn Arg
 1               5                  10                  15

Gln Leu Ser Leu
        20

<210> SEQ ID NO 7
<211> LENGTH: 20
<212> TYPE: PRT
<213> ORGANISM: Artificial Sequence
<220> FEATURE:
<223> OTHER INFORMATION: Synthetic peptide

<400> SEQUENCE: 7

His Phe Asp Tyr Met Ile Arg Asn Arg Thr Pro Tyr Tyr Gln Trp Pro
 1               5                  10                  15

Thr Val Gly Gln
        20

<210> SEQ ID NO 8
<211> LENGTH: 20
<212> TYPE: PRT
<213> ORGANISM: Artificial Sequence
<220> FEATURE:
<223> OTHER INFORMATION: Synthetic peptide

<400> SEQUENCE: 8

Arg Asp Arg Thr Gly Ala Val Val Gly Thr Gln Pro Pro Tyr Trp Leu
 1               5                  10                  15

Gly Ala Phe Arg
```

-continued

```
<210> SEQ ID NO 9
<211> LENGTH: 20
<212> TYPE: PRT
<213> ORGANISM: Artificial Sequence
<220> FEATURE:
<223> OTHER INFORMATION: Synthetic peptide

<400> SEQUENCE: 9

Gly Phe Trp Gly Met Glu His Asn Leu Thr Thr Gly Leu Ser Pro Thr
1               5                   10                  15

Trp Tyr Leu Lys
            20

<210> SEQ ID NO 10
<211> LENGTH: 20
<212> TYPE: PRT
<213> ORGANISM: Artificial Sequence
<220> FEATURE:
<223> OTHER INFORMATION: Synthetic peptide

<400> SEQUENCE: 10

Ser Trp Asn Leu Arg Ser Leu Pro Asp Gln Pro Ile Gly Ser Pro Pro
1               5                   10                  15

Pro Tyr Trp Leu
            20

<210> SEQ ID NO 11
<211> LENGTH: 20
<212> TYPE: PRT
<213> ORGANISM: Artificial Sequence
<220> FEATURE:
<223> OTHER INFORMATION: Synthetic peptide

<400> SEQUENCE: 11

Phe Ala Phe Lys Leu Gly Gly Asn Gly Leu Gly Gly Ala Thr Tyr Pro
1               5                   10                  15

Pro Tyr Phe Ile
            20

<210> SEQ ID NO 12
<211> LENGTH: 5
<212> TYPE: PRT
<213> ORGANISM: Artificial Sequence
<220> FEATURE:
<221> NAME/KEY: VARIANT
<222> LOCATION: 5
<223> OTHER INFORMATION: Xaa = Any Amino Acid
<220> FEATURE:
<223> OTHER INFORMATION: Synthetic peptide

<400> SEQUENCE: 12

Pro Pro Tyr Tyr Xaa
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic peptide

<400> SEQUENCE: 13

Pro Pro Tyr Tyr Leu
1               5
```

```
<210> SEQ ID NO 14
<211> LENGTH: 20
<212> TYPE: PRT
<213> ORGANISM: Artificial Sequence
<220> FEATURE:
<223> OTHER INFORMATION: Synthetic peptide

<400> SEQUENCE: 14

Lys Val Glu Leu Met Tyr Pro Pro Pro Tyr Tyr Leu Gly Ile Gly Asn
 1               5                  10                  15

Gly Thr Gly Gly
            20

<210> SEQ ID NO 15
<211> LENGTH: 20
<212> TYPE: PRT
<213> ORGANISM: Artificial Sequence
<220> FEATURE:
<223> OTHER INFORMATION: Synthetic peptide

<400> SEQUENCE: 15

Gly Gly Leu Val Met Ile Glu Arg Phe Asn Lys Leu Glu Leu Thr Trp
 1               5                  10                  15

Ala Asp Asp Asp
            20

<210> SEQ ID NO 16
<211> LENGTH: 20
<212> TYPE: PRT
<213> ORGANISM: Artificial Sequence
<220> FEATURE:
<223> OTHER INFORMATION: Synthetic peptide

<400> SEQUENCE: 16

Val Cys Ala Leu Pro Asp Val Gly Tyr Glu Phe Leu Thr Ser Asn Ala
 1               5                  10                  15

Asp Glu Pro Cys
            20

<210> SEQ ID NO 17
<211> LENGTH: 20
<212> TYPE: PRT
<213> ORGANISM: Artificial Sequence
<220> FEATURE:
<223> OTHER INFORMATION: Synthetic peptide

<400> SEQUENCE: 17

Tyr Leu Ala Asn His Phe Gly Trp Thr Ser Met Val Trp Asp Ala Asp
 1               5                  10                  15

Asp Thr Gly His
            20

<210> SEQ ID NO 18
<211> LENGTH: 20
<212> TYPE: PRT
<213> ORGANISM: Artificial Sequence
<220> FEATURE:
<223> OTHER INFORMATION: Synthetic peptide

<400> SEQUENCE: 18

Arg Asn Trp Ala Arg Arg Thr Ser Asn Leu Ser Trp Asp Gly Asp Asp
 1               5                  10                  15

Gly Ser Arg Gly
```

<210> SEQ ID NO 19
<211> LENGTH: 20
<212> TYPE: PRT
<213> ORGANISM: Artificial Sequence
<220> FEATURE:
<223> OTHER INFORMATION: Synthetic peptide

<400> SEQUENCE: 19

Thr Ala Glu Arg Cys Val Ser Leu Thr Trp Asn Asp Asp Thr Cys Asp
1               5                   10                  15

Leu Thr Gly Ala
            20

<210> SEQ ID NO 20
<211> LENGTH: 20
<212> TYPE: PRT
<213> ORGANISM: Artificial Sequence
<220> FEATURE:
<223> OTHER INFORMATION: Synthetic peptide

<400> SEQUENCE: 20

Phe Gly Leu Gln Ser Leu Cys Trp Glu Glu Asp Ala Gly Leu Val Phe
1               5                   10                  15

Gly Gln Asp Ser
            20

<210> SEQ ID NO 21
<211> LENGTH: 20
<212> TYPE: PRT
<213> ORGANISM: Artificial Sequence
<220> FEATURE:
<223> OTHER INFORMATION: Synthetic peptide

<400> SEQUENCE: 21

Asn Lys Glu Ser Leu Asn Trp Ala Asp Glu Leu Val Arg Lys Asp Pro
1               5                   10                  15

Pro His Gly Val
            20

<210> SEQ ID NO 22
<211> LENGTH: 20
<212> TYPE: PRT
<213> ORGANISM: Artificial Sequence
<220> FEATURE:
<223> OTHER INFORMATION: Synthetic peptide

<400> SEQUENCE: 22

Tyr Thr Glu Leu Thr Phe Ala Asn Asp Gly Leu Gly Ser Gly Lys Asn
1               5                   10                  15

Leu Ile Pro Lys
            20

<210> SEQ ID NO 23
<211> LENGTH: 20
<212> TYPE: PRT
<213> ORGANISM: Artificial Sequence
<220> FEATURE:
<223> OTHER INFORMATION: Synthetic peptide

<400> SEQUENCE: 23

Tyr Gly Ala Leu Thr Cys Phe Asn Asp Arg Ser Asp Cys Phe Phe Thr
1               5                   10                  15

```
Ser Pro Phe Ile
            20

<210> SEQ ID NO 24
<211> LENGTH: 20
<212> TYPE: PRT
<213> ORGANISM: Artificial Sequence
<220> FEATURE:
<223> OTHER INFORMATION: Synthetic peptide

<400> SEQUENCE: 24

His Leu Asn Trp Gly Glu Glu Val Arg His Gln Gly Glu Pro Arg Ala
1               5                   10                  15

Asp Gln Pro Phe
            20

<210> SEQ ID NO 25
<211> LENGTH: 20
<212> TYPE: PRT
<213> ORGANISM: Artificial Sequence
<220> FEATURE:
<223> OTHER INFORMATION: Synthetic peptide

<400> SEQUENCE: 25

His Leu Asn Trp Gly Glu Glu Val Arg His Gln Gly Glu Pro Arg Ala
1               5                   10                  15

Asp Gln Pro Phe
            20

<210> SEQ ID NO 26
<211> LENGTH: 20
<212> TYPE: PRT
<213> ORGANISM: Artificial Sequence
<220> FEATURE:
<223> OTHER INFORMATION: Synthetic peptide

<400> SEQUENCE: 26

Val Leu Thr Phe Leu Glu Arg Leu Leu Pro Ala Val Val Pro Arg Ser
1               5                   10                  15

Cys His Pro Gly
            20

<210> SEQ ID NO 27
<211> LENGTH: 20
<212> TYPE: PRT
<213> ORGANISM: Artificial Sequence
<220> FEATURE:
<223> OTHER INFORMATION: Synthetic peptide

<400> SEQUENCE: 27

Leu Ser Trp Gly Leu Glu Pro Trp Glu Gly Ser Phe Leu Trp Leu Thr
1               5                   10                  15

Glu Ser Pro Met
            20

<210> SEQ ID NO 28
<211> LENGTH: 20
<212> TYPE: PRT
<213> ORGANISM: Artificial Sequence
<220> FEATURE:
<223> OTHER INFORMATION: Synthetic peptide

<400> SEQUENCE: 28

Leu Asn Trp Asp Ile Asp Ser Met Pro Met Gly Val Tyr Cys Asp Val
1               5                   10                  15
```

```
Pro Asp Ser Cys
            20

<210> SEQ ID NO 29
<211> LENGTH: 6
<212> TYPE: PRT
<213> ORGANISM: Artificial Sequence
<220> FEATURE:
<223> OTHER INFORMATION: Synthetic peptide

<400> SEQUENCE: 29

Leu Thr Phe Leu Asp Asp
 1               5

<210> SEQ ID NO 30
<211> LENGTH: 18
<212> TYPE: PRT
<213> ORGANISM: Artificial Sequence
<220> FEATURE:
<223> OTHER INFORMATION: Synthetic peptide

<400> SEQUENCE: 30

Ala Ala Thr Tyr Met Met Gly Asn Glu Leu Thr Phe Leu Asp Asp Ser
 1               5                  10                  15

Ile Cys

<210> SEQ ID NO 31
<211> LENGTH: 12
<212> TYPE: DNA
<213> ORGANISM: Artificial Sequence
<220> FEATURE:
<223> OTHER INFORMATION: Oligonucleotide

<400> SEQUENCE: 31
ctttagagca ca                                                         12

<210> SEQ ID NO 32
<211> LENGTH: 8
<212> TYPE: DNA
<213> ORGANISM: Artificial Sequence
<220> FEATURE:
<223> OTHER INFORMATION: Oligonucleotide

<400> SEQUENCE: 32 ctctaaag                                                               8

<210> SEQ ID NO 33
<211> LENGTH: 46
<212> TYPE: PRT
<213> ORGANISM: Artificial Sequence
<220> FEATURE:
<221> NAME/KEY: VARIANT
<222> LOCATION: 1, 2, 3, 4, 5, 6, 7, 8, 9, 10, 11, 12, 13, 14, 15, 16,
      17, 18, 19, 20, 27, 28, 29, 30, 31, 32, 33, 34, 35, 36, 37,
      38, 39, 40, 41, 42, 43, 44, 45, 46
<223> OTHER INFORMATION: Xaa = Any Amino Acid
<220> FEATURE:
<223> OTHER INFORMATION: Synthetic peptide

<400> SEQUENCE: 33

Xaa Xaa Xaa Xaa Xaa Xaa Xaa Xaa Xaa Xaa Xaa Xaa Xaa Xaa Xaa Xaa
 1               5                  10                  15

Xaa Xaa Xaa Xaa Leu Thr Phe Leu Asp Asp Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa
```

```
         35                  40                  45

<210> SEQ ID NO 34
<211> LENGTH: 45
<212> TYPE: PRT
<213> ORGANISM: Artificial Sequence
<220> FEATURE:
<221> NAME/KEY: VARIANT
<222> LOCATION: 1, 2, 3, 4, 5, 6, 7, 8, 9, 10, 11, 12, 13, 14, 15, 16,
      17, 18, 19, 20, 26, 27, 28, 29, 30, 31, 32, 33, 34, 35, 36,
      37, 38, 39, 40, 41, 42, 43, 44, 45
<223> OTHER INFORMATION: Xaa = Any Amino Acid
<220> FEATURE:
<223> OTHER INFORMATION: Synthetic peptide

<400> SEQUENCE: 34

Xaa Xaa Xaa Xaa Xaa Xaa Xaa Xaa Xaa Xaa Xaa Xaa Xaa Xaa
 1               5                  10                  15

Xaa Xaa Xaa Xaa Pro Pro Tyr Tyr Leu Xaa Xaa Xaa Xaa Xaa Xaa
            20                  25                  30

Xaa Xaa Xaa Xaa Xaa Xaa Xaa Xaa Xaa Xaa Xaa
        35                  40                  45

<210> SEQ ID NO 35
<211> LENGTH: 561
<212> TYPE: DNA
<213> ORGANISM: Homo sapiens
<220> FEATURE:
<221> NAME/KEY: CDS
<222> LOCATION: (1)...(561)

<400> SEQUENCE: 35 gca atg cac gtg gcc cag cct gct gtg gta ctg gcc agc agc cga ggc      48
Ala Met His Val Ala Gln Pro Ala Val Val Leu Ala Ser Ser Arg Gly
 1               5                  10                  15 atc gcc agc ttt gtg tgt cag tat gca tct cca ggc aaa gcc act gag      96
Ile Ala Ser Phe Val Cys Gln Tyr Ala Ser Pro Gly Lys Ala Thr Glu
            20                  25                  30 gtc cgg gtg aca gtg ctt cgg cag gct gac agc cag gtg act gaa gtc     144
Val Arg Val Thr Val Leu Arg Gln Ala Asp Ser Gln Val Thr Glu Val
        35                  40                  45 tgt gcg gca acc tac atg atg ggg aat gag ttg acc ttc cta gat gat     192
Cys Ala Ala Thr Tyr Met Met Gly Asn Glu Leu Thr Phe Leu Asp Asp
    50                  55                  60 tcc atc tgc acg ggc acc tcc agt gga aat caa gtg aac ctc act atc     240
Ser Ile Cys Thr Gly Thr Ser Ser Gly Asn Gln Val Asn Leu Thr Ile
 65                  70                  75                  80 caa gga ctg agg gcc atg gac acg gga ctc tac atc tgc aag gtg gag     288
Gln Gly Leu Arg Ala Met Asp Thr Gly Leu Tyr Ile Cys Lys Val Glu
                85                  90                  95 ctc atg tac cca ccg cca tac tac ctg ggc ata ggc aac gga acc cag     336
Leu Met Tyr Pro Pro Pro Tyr Tyr Leu Gly Ile Gly Asn Gly Thr Gln
           100                 105                 110 att tat gta att gat cca gaa ccg tgc cca gat tct gac ttc ctc ctc     384
Ile Tyr Val Ile Asp Pro Glu Pro Cys Pro Asp Ser Asp Phe Leu Leu
       115                 120                 125 tgg atc ctt gca gca gtt agt tcg ggg ttg ttt ttt tat agc ttt ctc     432
Trp Ile Leu Ala Ala Val Ser Ser Gly Leu Phe Phe Tyr Ser Phe Leu
   130                 135                 140 ctc aca gct gtt tct ttg agc aaa atg cta aag aaa aga agc cct ctt     480
Leu Thr Ala Val Ser Leu Ser Lys Met Leu Lys Lys Arg Ser Pro Leu
145                 150                 155                 160 aca aca ggg gtc tat gtg aaa atg ccc cca aca gag cca gaa tgt gaa     528
```

```
Thr Thr Gly Val Tyr Val Lys Met Pro Pro Thr Glu Pro Glu Cys Glu
            165                 170                 175 aag caa ttt cag cct tat ttt att ccc atc aat                              561
Lys Gln Phe Gln Pro Tyr Phe Ile Pro Ile Asn
            180                 185

<210> SEQ ID NO 36
<211> LENGTH: 187
<212> TYPE: PRT
<213> ORGANISM: Artificial Sequence
<220> FEATURE:
<223> OTHER INFORMATION: Protein

<400> SEQUENCE: 36

Ala Met His Val Ala Gln Pro Ala Val Val Leu Ala Ser Ser Arg Gly
  1               5                  10                  15

Ile Ala Ser Phe Val Cys Gln Tyr Ala Ser Pro Gly Lys Ala Thr Glu
                 20                  25                  30

Val Arg Val Thr Val Leu Arg Gln Ala Asp Ser Gln Val Thr Glu Val
             35                  40                  45

Cys Ala Ala Thr Tyr Met Met Gly Asn Glu Leu Thr Phe Leu Asp Asp
         50                  55                  60

Ser Ile Cys Thr Gly Thr Ser Ser Gly Asn Gln Val Asn Leu Thr Ile
 65                  70                  75                  80

Gln Gly Leu Arg Ala Met Asp Thr Gly Leu Tyr Ile Cys Lys Val Glu
                 85                  90                  95

Leu Met Tyr Pro Pro Pro Tyr Tyr Leu Gly Ile Gly Asn Gly Thr Gln
            100                 105                 110

Ile Tyr Val Ile Asp Pro Glu Pro Cys Pro Asp Ser Asp Phe Leu Leu
            115                 120                 125

Trp Ile Leu Ala Ala Val Ser Ser Gly Leu Phe Phe Tyr Ser Phe Leu
        130                 135                 140

Leu Thr Ala Val Ser Leu Ser Lys Met Leu Lys Lys Arg Ser Pro Leu
145                 150                 155                 160

Thr Thr Gly Val Tyr Val Lys Met Pro Pro Thr Glu Pro Glu Cys Glu
            165                 170                 175

Lys Gln Phe Gln Pro Tyr Phe Ile Pro Ile Asn
            180                 185

<210> SEQ ID NO 37
<211> LENGTH: 43
<212> TYPE: DNA
<213> ORGANISM: Artificial Sequence
<220> FEATURE:
<223> OTHER INFORMATION: Oligonucleotide

<400> SEQUENCE: 37
gcagagagac atatggcaat gcacgtggcc cagcctgctg tgg                           43

<210> SEQ ID NO 38
<211> LENGTH: 50
<212> TYPE: DNA
<213> ORGANISM: Artificial Sequence
<220> FEATURE:
<223> OTHER INFORMATION: Oligonucleotide

<400> SEQUENCE: 38
gcagagagag gatcctcagt cagttagtca gaatctgggc acggttctgg                    50

<210> SEQ ID NO 39
```

```
<211> LENGTH: 107
<212> TYPE: DNA
<213> ORGANISM: Artificial Sequence
<220> FEATURE:
<223> OTHER INFORMATION: Oligonucleotide

<400> SEQUENCE: 39
ggcactagtc atgaaatacc tattgcctac ggcagccgct ggattgttat tactcgctgc      60
ccaaccagcg atggccgcag caatgcacgt ggcccagcct gctgtgg                  107
```